United States Patent
Altura et al.

(10) Patent No.: US 6,218,192 B1
(45) Date of Patent: *Apr. 17, 2001

(54) METHOD AND COMPOSITION FOR TREATMENT OF HEADACHE USING MAGNESIUM

(75) Inventors: Burton M. Altura; Bella T. Altura, both of Beechhurst; Alexander Mauskop, Larchmont, all of NY (US)

(73) Assignee: Research Foundation of the State University of New York, Albany, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/390,530

(22) Filed: Feb. 17, 1995

Related U.S. Application Data

(63) Continuation-in-part of application No. 07/864,646, filed on Apr. 7, 1992, now Pat. No. 5,460,972, which is a continuation-in-part of application No. 07/681,940, filed on Apr. 8, 1991, now abandoned.

(51) Int. Cl.$^7$ .................................................. G01N 33/20
(52) U.S. Cl. ............................ 436/79; 436/74; 424/677; 424/681; 424/682; 424/697
(58) Field of Search ....................... 436/74, 79; 424/677, 424/681, 682, 697

(56) References Cited

U.S. PATENT DOCUMENTS

| | | | | |
|---|---|---|---|---|
| 3,009,859 | * | 11/1961 | Leborit | 167/65 |
| 3,359,166 | * | 12/1967 | McClure | 167/65 |
| 3,759,980 | * | 9/1973 | Rosen et al. | 260/480 |
| 3,865,933 | * | 2/1975 | Mudge | 424/153 |
| 4,083,951 | * | 4/1978 | Goudie et al. | 424/44 |

(List continued on next page.)

OTHER PUBLICATIONS

Mauskop et al. "Deficiency in Serum Ionized Magnesium but not Total Magnesium in Patients w/Migraines. Possible Role of ICa$^{2+}$/IMg$^{2+}$ Ratio." Headache, 33, 3, 1993, pp. 135–138.*

Weaver "Magnesium & Migraine"; Letter to the Editor, Feb. 1990, p. 168.*

Opavsky "Magnesium & Its Composition w/Cinnarizine in the Long–Term Treatment of Headache." Acte Universitetis Palackiance Olomucensis Facultatis Medicac, 1991, 131, pp. 157–164.*

D'Addesio "Post Partum Eclampsia" Annals of Emergency Medicine, 1989, 18, 10 pp. 1105–1106.*

Danielson, et al., "The Determination of Ultrafilterable Calcium and Magnesium in Serum", *Upsala J. of Med. Science*, vol. 87, p. 43–53 (1982).

(List continued on next page.)

*Primary Examiner*—S Carrillo
(74) *Attorney, Agent, or Firm*—Morgan & Fannegan, L.L.P.

(57) ABSTRACT

A method of treating headache is provided using a water soluble magnesium salt. Specifically, a method of treating a headache is provided for an individual having a serum ionized magnesium concentration of 0.44 mmoles/L to 0.53 mmoles/L and having at least one headache symptom by administering an amount of a water soluble magnesium salt sufficaent to inhibit at least one headache symptom in the individual within 24 hours and to raise the serum ionized magnesium concentration in the individual to within a normal ionized magnesium concentration range of 0.54 mmoles/L to 0.67 mmoles/L. Headache symptoms which may be inhibited include: pain, aura, photophobia, nausea, unilateral pain and phonophobia.

7 Claims, 6 Drawing Sheets

U.S. PATENT DOCUMENTS

| | | | |
|---|---|---|---|
| 4,346,106 | * 8/1982 | Sudilovsky | 424/311 |
| 4,448,770 | 5/1984 | Epting | 424/153 |
| 4,563,465 | * 1/1986 | Fozard et al. | 514/304 |
| 4,670,285 | 6/1987 | Clandinin et al. | 426/602 |
| 4,752,479 | 6/1988 | Briggs et al. | 424/472 |
| 4,954,349 | 9/1990 | Sheth et al. | 424/461 |
| 5,053,396 | * 10/1991 | Blass | 514/45 |
| 5,108,767 | 4/1992 | Mulchandani et al. | 426/72 |
| 5,273,759 | * 12/1993 | Simmons | 424/465 |
| 5,364,642 | * 11/1994 | Altura et al. | 426/74 |
| 5,460,972 | * 10/1995 | Altura et al. | 436/79 |
| 5,478,577 | * 12/1995 | Sackler et al. | 424/489 |
| 5,536,959 | * 7/1996 | Mauskop | 514/165 |
| 5,872,145 | * 2/1999 | Plachetka | 514/415 |

OTHER PUBLICATIONS

Bella T. Altura, et al., Clinical Studies with the NOVA ISE for $IMg^{2+}$, Scan. J. Lab. Clin. Invest. Suppl. (Norway), vol. 217, p. 53–67 (1994).

Emanuel Lebenthal, M.D., "Textbook of Gstroenterology and Nutrition in Infancy", Errors in Formula Design and Manufacture, pp. 438–448, Chapter 35.

Niels Fogh–Anderson, et al, Ionic Binding, Net Change, and Donnan Effect of Human Serum Albumin as a Function of pH, Clin. Chem., 38/1, 48–52 (1993).

Oesch, U., et al., "Ion–Selective Membrane Electrodes for Clinical Use", Clin. Chem., 32/8, 1448–1459 (1986).

Dinten, O. et al., "Lifetime of Neutral–Carrier–Based Liquid Membranes In Hqueous Samples and Blood and the Lipophilicity of Membrane Components", Anal. Chem. 63, pp. 596–603 (1991).

MacFate, R.P., "Introduction to the Clinical Laboratory", Year Book Medical Pub., Inc., Chicago, pp. 257–259 (1972).

Henry, J.G., "Chapter 9 Clinical Chemistry", In: Clinical Diagnosis by Laboratory Methods 15th Edition, Editors: I. Davidsohn and J.B. Henry, W.B. Saunders Co., Philadelphia, pp. 516–524 (1974).

Mauskop, A. et al., "Deficiency in Serum Ionized Magnesium but not Total Magnesium in Patients With Migraines. Possible Role of $ICa^{2+}/IMg^{2+}$ Ration", Headache Journal, vol. 33, No. 3, pp. 135–138 (Mar. 1993).

Handwerker, S.M. et al., Ionized Magnesium and Calcium Levels in Umbilical Cord Serum of Pregant Women With Transient Hypertension During Labor, American Journal of Hypertension, vol. 6, pp. 542–545 (1993).

Altura, B.T. et al., "A new Method for the Rapid Determination of Ionized $Mg^{2+}$ in Whole Blood, Serum and Plasma", Meth. Find. Exp. Clin. Pharmacol., vol. 14 No. 4, pp. 297–304 (1992).

Altura, B.J. et al., "Measurement of Ionized Magnesium in Whole Blood, Plasma and Serum With a new Ion–selective Elctrode in Healthy and Diseased Human Subjects", Magnes Trace Elem., vol. 10, pp. 90–98 (1992).

Altura, B.M. et al., "Magnesium Ions and Contraction of Vascular Smooth Muscles: Relationship to Some Vascular Disease", Federation Proceedings, vol. 40 No. 12, pp. 2672–2679 (Oct. 1981).

Altura, B.M. et al., "Magnesium Deficiency and Hypertension Correlation Between Magnesium–Deficient Diets and Microcirculatory Changes in Situ", Science, vol. 223, pp. 1315–1317 (Mar. 23, 1984).

Walser, M., Ion Association. VI. Interactions Between Calcium, Magnesium, Inorganic Phosphate, Citrate and Protein in Normal Human Plasma. J. Clin. Investigation, vol. 40, pp. 723–730 (Jan.–Jun. 1961).

Resnick, L.M.; Gupta, R.K.; Laragh, J.H.; Alderman, M.H.; Altura, B.M., "Intracellular and extracellular magnesium depletion in Type 2 (non–insulin–dependent) diabetes mellitus". Diabetologia (1993) 36: 767–770.

Handwerker, Sara M., M.D.; Altura, Bella T., Ph.D.; Royo, Blas, M.D.; and Altura, Burton M., Ph.D., "Ionized Serum Magnesium Levels in Umbilical Cord Blood of Normal Pregnant Women at Delivery: Relationship to Calcium, Demographics, and Birthweight". American Journal of Perinatology, vol. 10, No. 5, pp. 392–397 (Sep. 1993).

Altura, Burton M.; Altura, Bella T.; and Gupta, Raj K., "Alcohol Intoxication Results in Rapid Loss in Free Magnesium in Brain and Disturbances in Brain Bioenergetics: Relation to Cerebrovasospasm, Alcohol–Induced Strokes, and Barbiturate Anesthesia–Induced Deaths". Magnesium and Trace Elements, 1991–92; 10: 122–135.

Mauskop, Alexander; Altura, Bella T.; Cracco, Roger Q.; and Altura Burton M., "Serum Ionized Magnesium Levels in Patients with Tension–type Headaches". Tension–type Headache: Classification, Mechanisms, and Treatment, ed. by J. Olsen and J. Schoenen. Raven Press. Ltd., New York, pp. 137–140 (1993).

Altura, B.M. and Altura B.T., "Cardiovascular Risk Factors and Magnesium: Relationship to Atherosclerosis, Ischemic Heart Disease and Hypertension". Magnesium and Trace Elements, 1991–92; 10: 182–192.

Wybenga, DR, et al. "Determination of Ionized Calcium in Serum That has Been Exposed to air", Clin. Chem. 22/7, p. 1009–1011, 1976.

Wortsman, J., et al., "A Rapid Method for the Determination of Ultrafilterable Calcium in Serum", J. Lab. Clin. Med. 98(5), p. 691–696, 1981.

Markell, M.S.; Altura, B.T.; Barbour, R.L.; and Altura, B.M. "Ionized and total magnesium levels in cyclosporin–treated renal transplant recipients: relationship with cholesterol and cyclosporin levels". Clinical Science (1993) 85, 315–318.

N. Fogh–Andersen et al, Ionized Calcium During Dialysis and Ultrafiltration, Scand. J. Clin. Lab. Invest., 43, Suppl. 165, 39–41 (1983).

Maier, H., et al., "Investigations on the performance of Calcium Selective Disc–Electrodes With Electrically Charged and Neutral Ligands in Anaerobic Serum Measurements", Res. Exp. Med. (Berl),, 172/1, p. 75–81 (1978) (English Abstract only).

Maj–Zurawska, M. et al., "Fully automated potentiometric determination of ionized magnesium in blood serum", Analytical Chimica Actu, 236 (1990) p. 331–335.

Altura, B.M., "Calcium Antagonist Properties of Magnesium: Implications for Antimigraine Actions", Magnesium, 1985, 4:169–175 (1985).

Ramadan, M.M. et al, "Low Brain Magnesium in Migraine", Headache, 1989; 29:590–593.

Mody, I. et al, "Low Extracellular Magnesium Induces Epileptiform Activity and Spreding Depression In Rat Hippocampal Slices", J. Neurophysiol, 1987, 57:869–888.

Weaver, K. "Magnesium and Migraine: Reversible Hypomagnesic Coagulative Antiopathy, Hypothesis and Preliminary Data" (Abstract), J. Am. Coll. Nutr., 1983, 2:287–288.

Facchinetti, F. et al, "Magnesium Prophylaxis of Menstrual Migraine: Effects On Intracellular Magnesium", *Headache*, 1991, 31:298–301.

Sarchielli, et al, "Serum and Salivary Magnesium Levels in Migraine and Tension–Type Headache. Results in a Group of Adult Patients", *Cephalalgia*, 1992, 12:21–27.

Schoenen, J. et al, "Blood Magnesium Levels in Migraine", *Cephalalgia*, 1991, 11:97–99.

Gallai, V. et al, Magnesium Content of Mononuclear Blood Cells in Migraine Patients, *Headache*, 1994; 34:160–165.

Mauskop, A. et al, "Chronic Daily Headache—One Disease or Two. Diagnostic Role of Serum Ionized Magnesium", *Cephalalgia*, 1994, 14:24–28.

Mauskop, A. et al, "Serum Ionized Magnesium ($Mg^{2+}$) Levels in Patients (P) with Episodic and Chronic Cluster Headaches (CH)", *Clin. Pharm. Ther.*, 53 (2):227, 1993 (Abstract).

Pfaffenrath, V., "Chronic Daily Headache", *Cephalalgia*, 1993, 13 (Suppl 12):66–67.

Altura, B.T. et al, "The Role of Magnesium in Etiology of Strokes and Cerebrovasospasm", *Magnesium* 1982, 1:277–291.

Altura, B.T. "Comparative Effects of a Mg–Enriched Diet and Different Orally Administered Magnesium Oxide Preparations on Ionized Mg, Mg Metabolism and Electrolytes in Serum of Human Volunteers", *J Am. Coll. Nutrition*, 1994, 13:447–454.

* cited by examiner

METHOD AND COMPOSITION FOR TREATMENT OF HEADACHE USING MAGNESIUM

This application is a continuation-in-part of pending U.S. Ser. No. 07/864,646, filed Apr. 7, 1992 which issued U.S. Pat. No. 5,460,972 which is a continuation-in-part of pending U.S. Ser. No. 07/681,940 filed Apr. 8, 1991 abandoned.

BACKGROUND ART

Magnesium (Mg) is the second most abundant cation in the body [Altura, B. M. et al., Drugs 28 (Suppl.I):120–142, 1984]. It is cofactor for more than 325 cellular enzymes involved in cellular energy production and storage, protein synthesis, DNA and RNA synthesis, cell growth and reproduction, adenylate cyclase synthesis, maintenance of cellular electrolyte composition, and stabilization of mitochondrial membranes [Altura, B. M. et al, Drugs 28 (Suppl.I):120–142, 1984; Wacker, W. E. C. *Magnesium and Man,* Harvard Univ. Press, Cambridge, 1980]. As a consequence of these biochemical activities, Mg plays a pivotal role in control of neuronal activity, cardiac excitability, neuromuscular transmission, muscular contraction, and vasomotor tone [Altura, B. M. et al., Drugs 28 (Suppl.I):120–142, 1984; Wacker, W. E. C. *Magnesium and Man,* Harvard Univ. Press, Cambridge, 1980; Altura, B. M. et al., in: *Metal Ions in Biological Systems,* ed. by H. Sigel and A. Sigel, Vol 26: Compendium on Magnesium and Its Role in Biology, Nutrition, and Physiology, pp 359–416, Marcel Dekker, Inc. New York, 1990].

Most clinical data of Mg determinations are derived from blood levels of total Mg (Wacker, W. E. C. *Magnesium and Man,* 1980; Elin, R. J. Clin. Chem. 33:1965–1970, 1987). Total serum Mg concentrations reflect protein-bound (30–40%), chelated (7–12%), and free or ionized Mg ($Mg^{2+}$) (60–70%) fractions. The exact proportion of these fractions has been extremely difficult to determine precisely, and, moreover, there is no way to rapidly make such determinations. Precise information about Mg activity is pivotal to our understanding of Mg metabolism. The free or ionized form ($Mg^{2+}$) is the active form of the mineral (Wacker, W. E. C. *Magnesium and Man,* 1980; Elin, R. J. Clin. Chem. 33:1965– 1970, 1987; Ryan, M. F. Ann. Clin. Biochem. 28:19–26, 1991). Alterations in circulating protein levels (primarily albumin), which are seen in numerous pathophysiologic states, will alter the interpretation of Mg status (very similar to calcium) (Elin, R. J. Clin. Chem. 33:1965–1970, 1987).

Although numerous methods are available clinically, to determine total Mg in serum, plasma, urine, cerebral spinal fluid and other body fluids (e.g., atomic absorption spectrophotometry, atomic emission spectrophotometry, colorimetry, fluorometry, compleximetry and chromatograph for quantifying total Mg), none of these can determine ionized or free $Mg^{2+}$ (Elin, R. J. Cin. Chem. 33:1965–1970, 1987; Wills, M. R. et al. Magnesium 5:317–327, 1986).

Until the present invention, the only method for assessing free $Mg^{2+}$ in biological samples was an ultrafiltration procedure (Wacker, W. E. C. *Magnesium and Man,* 1980; Elin, R. J. Clin. Chem. 33:1965–1970, 1987; Wills, M. R. et al. Magnesium 5:317–327, 1986; Aikawa, J. K. *Magnesium: Its Biologic Significance,* CRC Press, Boca Raton, 1981). While this procedure is capable of measuring free $Mg^{2+}$, it is fraught with a multiplicity of problems (need to control pH, need to control filter composition, time-consuming, inability to access whole blood $Mg^{2+}$, need for centrifugation of blood). In addition, and most important, these classical methods, which primarily depend upon modifications of the procedure outlined by Watchorn, E. et al. (Biochem. J. 26:54, 1932), Toribara et. al. (J. Clin. Invest. 36:738, 1957) and Walser, M. (J. Clin. Invest. 40:723–730, 1961) result in ionized $Mg^{2+}$ values on normal subjects which are significantly different from those obtained by the present method as assessed using an ion selective electrode (ISE). Using ultracentrifugation methods combined with ultrafiltration methods to assess free $Mg^{2+}$, the percentages of ultrafilterable Mg reported by previous workers (around 70%) (Cummings, N. A. et al. Anal. Biochem 22:108–116, 1968; Nielson, S. P. Scand. J. Clin. Lab. Invest. 23:219–225, 1960) are much higher than the values using the present method. Even more recent measurements, using ultrafiltration and a micropartition filtration system has yielded a much wider range of values for ultrafilterable Mg from normal human subjects than those of the present method (D'Costa, M. et al. Clin. Chem. 29:519, 1983; Zaloga, G. P. et al. Crit. Care Med. 15:813–816, 1987). Some of these pitfalls preclude determination of $Mg^{2+}$ in various body fluids. Moreover, determinations can not be done on less than 1.0 ml of blood.

The physiologic or pathophysiologic effects of mild to severe (or graded) decreases or increases in extracellular free $Mg^{2+}$ in whole blood, serum or plasma has not been possible to discern in human subjects or animals either rapidly (e.g., within 1–2 min) or repeatedly (multiple samples over a few minutes-hours). Since Mg is frequently used in normomagnesemic patients for its antiarrhythmic, vasomotor and neuronal actions [Altura, B. M. et al. Drugs 28(Suppl.I):120–142, 1984; Wacker, W. E. C. *Magnesium and Man,* 1980; Altura, B. M. et.al. In: *Metal Ions in Biological Systems,* 1990; Iseri C. T. et al. West J. Med. 138:823–828, 1983; Ebel, H. et al. J. Clin. Chem. Clin. Biochem. 21:249–265, 1983], it is vital to be able to assess the exact extracellular level of ionized $Mg^{2+}$ at any one instant. Although there is a dire need to carefully monitor extracellular $Mg^{2+}$ in hypomagnesemic patients or patients linked to Mg deficiency states such as cardiovascular insufficiency, cardiac arrhythmias, coronary artery spasm, those at risk for sudden death, renal disorders, respiratory muscle weakness, pre-eclampsia, eclampsia, migraine, hypertension, premenstrual syndrome, tetany, seizures, tremor, apathy, depression, hypokalemia and hypocalcemia, there is at present no way to do this either precisely or rapidly [Altura, B. M. et al. Drugs 28(Suppl.I):120–142, 1984; Wacker, W. E. C. *Magnesium and Man,* 1980; Altura, B. M. et.al. In: Metal Ions in Biological Systems, 1990; Iseri, C. T. West J. Med. 138:823–828, 1983; Ebel, H. et al. J. Clin. Chem. Clin. Biochem. 21:249–265, 1983;Altura, B. M. et al. Magnesium 4:226–244, 1985; Zaloga, G. P. Chest 56:257–258, 1989; Sjogren, A. J. Intern. Med. 226:213–222, 1989; Zaloga, G. P. et al. In: *Problems in Critical Care,* ed. G. P. Zaloga Vol 4:425–436, J.B. Lippincott Co., Philadelphia, 1990; Resnick, L. M. et al. Proc. Nat. Acad. Sci. U.S.A. 81:6511–6515, 1984; Rudnick, M. et al. APMIS 98:1123–1127, 1990].

In 1980, it was suggested on the basis of in-vitro experiments that drops in ionized serum $Mg^{2+}$ would produce coronary vasospasm, arrhythmias and sudden death (Turlapaty and Altura, Science 208:198–200, 1980). Although clinical observations from other workers in the intervening years have suggested this might be a "real" possibility, up until the present invention, no evidence could be gathered due to the unavailability of a method for accurate and rapid assessment of blood ionized $Mg^{2+}$ (Altura, B. M. et al. In: *Metal Ions in Biological Systems,* Vol 26, 1990; Ebel, H. et al. J. Clin. Chem. Clin. Biochem. 21:249–265, 1983; Altura, B. M. et al. Magnesium 4:226–244, 1985; Sjogren, A. et al. J. Intern. Med. 226:213–222, 1989; Zaloga, G. P. et al. In: Problems In Critical Care Vol 4, 1990).

Over the past 10 years, it has been determined that reductions in ionized $Mg^{2+}$, experimentally in animals and isolated cerebral blood vessels, can induce intense vasospasm and rupture of blood vessels in the brain (Altura, B. M. et al. In: *Metal Ions in Biological Systems* Vol 26, 1990; Altura, B. T. et al.Neuroscience Letters 20:323–327, 1980; Altura, B. T. et al. Magnesium 1:277–291, 1982; Altura, B. T. et al. Magnesium 3:195–211, 1984; Altura, B. M. et al. Am. J. Emerg. Med. 1:180–193, 1983; Huang, Q-F., et al. FASEB J. 3:A845, 1989). On the basis of such experimental findings, it has been hypothesized that head trauma would be associated with deficits in serum, plasma and whole blood ionized $Mg^{2+}$ (Altura, B. T. et al. Magnesium 1:277–291, 1982; Altura, B. T. et al. Magnesium 3:195–211, 1984; Altura, B. M. et al. Am. J. Emerg. Med. 1:180–193, 1983). The present inventions has allowed these studies to be undertaken for the first time.

In the 1970's and 1980's, on the basis of numerous animal experiments, it was reported that deficits in ionized $Mg^{2+}$ would result in maintained peripheral vasospasm, constriction of small blood vessels in numerous organ regions and as a consequence development of high blood pressure or hypertension (Altura, B. M. et al. Drugs 28 (Suppl.I): 120–142, 1984; Altura, B. M. et al. In: *Metal Ions in Biological Systems* Vol 26, 1990; Altura, B. M. et al. Magnesium 4:226–244, 1985; Sjogren, A. et al. J. Intern. Med. 226:213–222, 1989; Turlapaty, P. D. M. V. et al. Science 208:198–200, 1980; Altura, B. M. et al. Federation Proc. 40:2672–2679, 1981; Altura, B. M. et al., Science 221:376–378, 1983; Altura, B. M. et al. Science 223:1315–1317, 1984). Until the development of the present invention, this hypothesis was not testable because of a lack of proper methodology for processing samples and measuring ionized $Mg^{2+}$.

Accelerated atherosclerotic heart disease is a leading cause of death in the long-term (>10 year) renal transplant recipient. Hypertension and hyperlipidemia are common in this population and may be secondary to cyclosporine use. Cyclosporine has been associated with a renal tubular total magnesium (Twg) leak, as evidence by low serum total magnesium values and increased urinary excretion. Hypomagnesemia has been implicated as a factor in modulation of blood lipid levels, alteration of vascular tone and cyclosporine toxicity. Until the present invention, accurate measurements of biologically active ionized magnesium or ionized $Ca^{2+}$/ionized $Mg^{2+}$ ratios were not possible. Therefore, until the present invention, it was not possible to determine the ratio of ionized calcium and ionized magnesium in hypercholesterolemia and cyclosporine toxicity in renal transplant recipients.

In 1981–1983, studies on isolated blood vessels from animals and pregnant women, suggested that reduction in dietary intake of Mg or inability to metabolize Mg properly could result in reduction in ionized $Mg^{2+}$ and thus in umbilical and placental vasospasm, possibly reducing oxygen and nutrients to the growing fetus (Altura, B. M. et al. Federation Proc. 40:2672–2679, 1981; Altura, B. M. et al., Science 221:376–378, 1983). The end result could be, in large measure, responsible for fetal growth retardation, pre-eclampsia, hypertension and convulsions, particularly in pregnant indigent women (Rudnick, M. et al. APMIS 98:1123–1127, 1990; Altura, B. M. Science 221:376–378, 1983). Mg has been recommended as early as 1925 in this country for treatment and prevention of pregnancy-induced pre-eclampsia, hypertension and convulsions, but a method for accurately monitoring ionized $Mg^{2+}$ rapidly and repeatedly throughout pregnancy was not available until development of the present invention.

National population statistics indicate that 18 million women and 5.6 million men suffer from severe migraine headaches.[1] Only about one-third of all headache patients are fully satisfied with treatments currently available.

Although major advances have been made in unraveling the etiologies of numerous disease states, the precise cause (s) of migraine headaches remains elusive. Many investigators suspect that migraine and tension-type headaches may be part-and-parcel of a similar biologic process despite having differing clinical symptoms.[2-4] One popular theory is that although a susceptible individual may first demonstrate intermittent migraines, these will evolve into chronic daily headaches, similar in nature to tension-type headaches, suggesting that possibly the two types of headaches derive from a similar initiating biochemical etiology. Another leading theory is that all headaches share a common neurotransmitter dysfunctional mechanism, for example, related to the actions of serotonin. Changes in magnesium levels have effects on the functions of serotonin,[27-29] and NMDA receptors,[30-32] nitric oxide production,[33] catecholamine production and activity[24] and on more than 325 enzymatic processes in the body.[35] I$Mg^{2+}$ levels are known to affect entry of $Ca^{2+}$, intracellular $Ca^{2+}$ levels and its release from sarcoplasmic and endoplasmic reticulum membranes in vascular muscle and endothelial cells which in turn control vascular tone and vascular reactivity to endogenous hormones and neurotransmitters.[36, 37] Such vascular effects could play a role in migraine pathogenesis.[5] Thus, magnesium deficiency could be involved in both the vascular and neurological aspects (e.g., migraine aura, pain, nausea, etc.) of the development of migraines.

Since 60 percent of all migraine sufferers report that close relatives often have a similar problem, it would appear that genetic control mechanisms are also important in several types of headaches. It is thus possible that, biochemically, there may be a common factor to the above enigma. A reliable biologic marker(s) for headache has long-remained elusive.[4]

A large body of circumstantial evidence points to the possible role of magnesium deficiency in the pathogenesis of headaches and a possible vascular mechanism has been proposed.[5] It was pointed out there that all drugs which have been successfully utilized for the treatment or prevention of migraine attacks acts on cerebral blood vessels. Cerebral blood vessels are more sensitive to Mg (either, deficient or excess of) than any other type of vascular muscle cells; Mg deficiency resulting in contraction and potentiation of vasoconstrictors and excess resulting in vasodilatation and inhibition of vasoconstrictors.[5, 6, 38] Deficiency in $Mg^{2+}$ in neuronal and vascular tissue could be expected to result in elevation in levels of catecholamines, serotonin, prostaglandins and substance P,[34, 35, 38-41] vasoactive substances long implicated in the etiology of migraine.[5] In addition, serotonin is known to be released form platelets during a migraine attack,[42] and to be a potent cerebral vasoconstrictorl and promote nausea and vomiting.[43] Some prostanoids, e.g., $PGE_1$, are known to provoke pulsating headaches and additional migraine-like symptoms[44] as well as potentiate vasoconstrictor hormones acting on blood vessels.[45] Pain in headache is often attributed to the action of substance P on sensory fibers.[46] It is of some interest to note that an Mg-deficiency induced state has recently been shown experimentally to result in significant generation and release of substance P into the blood stream.[41] Excess Mg is known to attenuate and inhibit the production and actions of substance P, serotonin and catecholamines on several types of end-organs including cerebral vascular tissue.[5,32,33,36,38]

Since 1960,[47] it has been known that $Mg^{2+}$ can prevent spreading depression in the cerebral cortex. This spreading depression causes an attenuation of blood flow to the affected area of the brain, resulting in local hypoxia and possibly the neurological phenomenon termed the aura of migraine. It has been suggested that the type A stressful personality, often seen in the old characteristic descriptions of migraine sufferers, is associated with a Mg deficit.[48] The fact that most Americans exhibit shortfalls in Mg intake in their daily diets,[34,35] and that some normal healthy volunteers exhibit deficits in serum $IMg^{2+}$ but not TMg,[49] supports the notion the Mg deficiency could be an important factor in the etiology of headaches.

Mg seems to possess unique weak calcium channel-blocking abilities.[5,35,36] It can act to regulate the entry of $Ca^{2+}$ into smooth muscle and endothelial cells,[35,36,50,51] and regulate the intracellular release and binding of $Ca^{2+}$ [35,40,51] by acting on potential-operated, receptor-operated and leak-operated $Ca^{2+}$ channels in these cells.[36] This may also help to explain why calcium channel blockers (CCB), unlike $Mg^{2+}$ shown here, require a relatively long period of therapy (e.g., two-to-five months) to achieve reasonable therapeutic effects in migraine sufferers.[52] CCB could not be expected to act on leak-operated $Ca^{2+}$ channels and only certain ones act on receptor-operated $Ca^{2+}$ channel, making $Mg^{2+}$ a potentially ideal therapeutic agent for headaches.[31]

[31]P-nuclear magnetic resonance spectroscopy showed low brain $Mg^{2+}$ in a limited number of subjects during and between migraine attacks.[6] A low $Mg^{2+}$ level is known to facilitate the development of spreading depression of Leao in animal experiments.[7] This phenomenon is thought to underlie the phenomenon of migraine aura. Several anecdotal observations and one double-blind, placebo controlled trial suggested that oral Mg supplementation may be helpful in some headache patients. Oral magnesium supplementation trials, for the treatment of headaches,[9-12] may have been impeded in the past by two factors. Absorption of oral supplements is highly variable and $IMg^{2+}$ levels were not monitored. One study reported that total serum Mg (TMg) levels were decreased in patients with migraine and tension-type headaches during an attack more than in the interictal period.[13] Two other studies showed normal serum levels of TMg between attacks of migraine.[12, 14] In one of these studies, a decreased TMg concentration in erythrocytes was found,[14] while in the other a decreased TMg concentration in lymphocytes and polymorphonuclear cells, but not erythrocytes, was detected. A recent study showed decreased TMg content in mononuclear cells in migraine patients with and without aura during an interictal period.[15]

Studies of $IMg^{2+}$ in large numbers of headache patients showed different incidences of low $IMg^{2+}$ levels in patients with different headache syndromes. Patients with chronic tension headaches[19] had the lowest incidence (4.5%), while patients with episodic cluster headaches had a 50% incidence.[20] Patients with an acute migraine headache had a 42% incidence of low $IMg^{2+}$ levels. Total magnesium levels in most of these patients, including those with low serum $IMg^{2+}$, were normal.[19-22]

The present invention is a novel treatment and composition that results in rapid and immediate relief of various types of headaches using magnesium.

A novel method to draw, handle, process and store biological samples for accurate, rapid and reproducible levels of ionized or free $Mg^{2+}$ was developed. The method of collecting and processing samples has utility in preparing biological samples for measurement of ionized $Mg^{2+}$ concentrations using a novel selective ion electrode with neutral carrier based membrane. Using the methods of the present invention, an accurate normal range for ionized $Mg^{2+}$ in whole blood, plasma and serum has been determined for the first time. It is now possible to diagnose, prognoses and treat various disease states by the method of the present invention, by monitoring fluctuations in ionized $Mg^{2+}$ concentrations.

SUMMARY OF INVENTION

The present invention relates to a method for preparing biological samples, including collection and storage conditions, prior to testing for ionized $Mg^{2+}$ concentrations under conditions which minimize or prevent exchange of gases between the biological sample and atmospheric air and in which air and $O_2$ is substantially excluded from the biological sample, preferably under anaerobic conditions, prior to measuring ionized $Mg^{2+}$.

Another aspect of the invention is a method for determining ionized $Mg^{2+}$ concentrations in a biological sample, collected and maintained under anaerobic conditions or conditions which minimize or prevent exchange of gases between the biological sample and atmospheric air and in which $O_2$ is substantially excluded from the biological sample, the $Mg^{2+}$ concentration being measured using an ion selective electrode with a neutral carrier based membrane.

Another aspect of the invention is a method for determining ionized $Ca^{2+}:Mg^{2+}$ ratios in a biological sample, collected and maintained under anaerobic conditions or conditions which minimize or prevent exchange of gases between the biological sample and atmospheric air and in which $O_2$ is substantially excluded from the biological sample, the $Ca^{2+}$ and $Mg^{2+}$ concentrations being measured using ion selective electrodes with a neutral carrier based membrane.

An additional aspect of the invention is a method for diagnosing or prognosing disease states such as headache, cardiac diseases, hypertension, idiopathic intracranial hypertension, diabetes, lung diseases, abnormal pregnancy, pre-eclampsia, eclampsia, head trauma, fetal growth retardation, and the like, in a patient using a method of determining ionized $Mg^{2+}$ concentrations or ionized $Ca^{2+}:Mg^{2+}$ ratios.

A further aspect of the invention is a method of maintaining normal ionized $Mg^{2+}$ concentrations in a patient in need of such maintenance comprising administration of $Mg^{2+}$ in the form of a pharmaceutical composition or dietary supplement. Another aspect of the invention is a method of maintaining normal ionized $Ca^{2+}$/ionized $Mg^{2+}$ molar ratios in an individual comprising administration of an effective amount of $Ca^{2+}$ and $Mg^{2+}$ in the form of a pharmaceutical composition or dietary supplement.

Another object of the present invention is a method and composition for treatment of headaches using a magnesium salt. The composition may be provided in a kit form along with a self-injection device.

Another aspect of the invention is a pharmaceutical composition or dietary supplement for preventing or treating magnesium deficiencies, the composition comprising as the active ingredient(s) a concentration of bioavailable magnesium or bioavailable calcium and magnesium, wherein the concentration(s) provides a normal physiological molar ratio of ionized $Ca^{2+}/Mg^{2+}$ in the body fluids, such body fluids comprising whole blood, serum, plasma, cerebral spinal fluid or the like.

BRIEF DESCRIPTION OF DRAWINGS

These and other objects, features, and many of the attendant advantages of the invention will be better understood upon a reading of the following detailed description when considered in connection with the accompanying drawings wherein.

DISCLOSURE OF INVENTION

Figure 1:
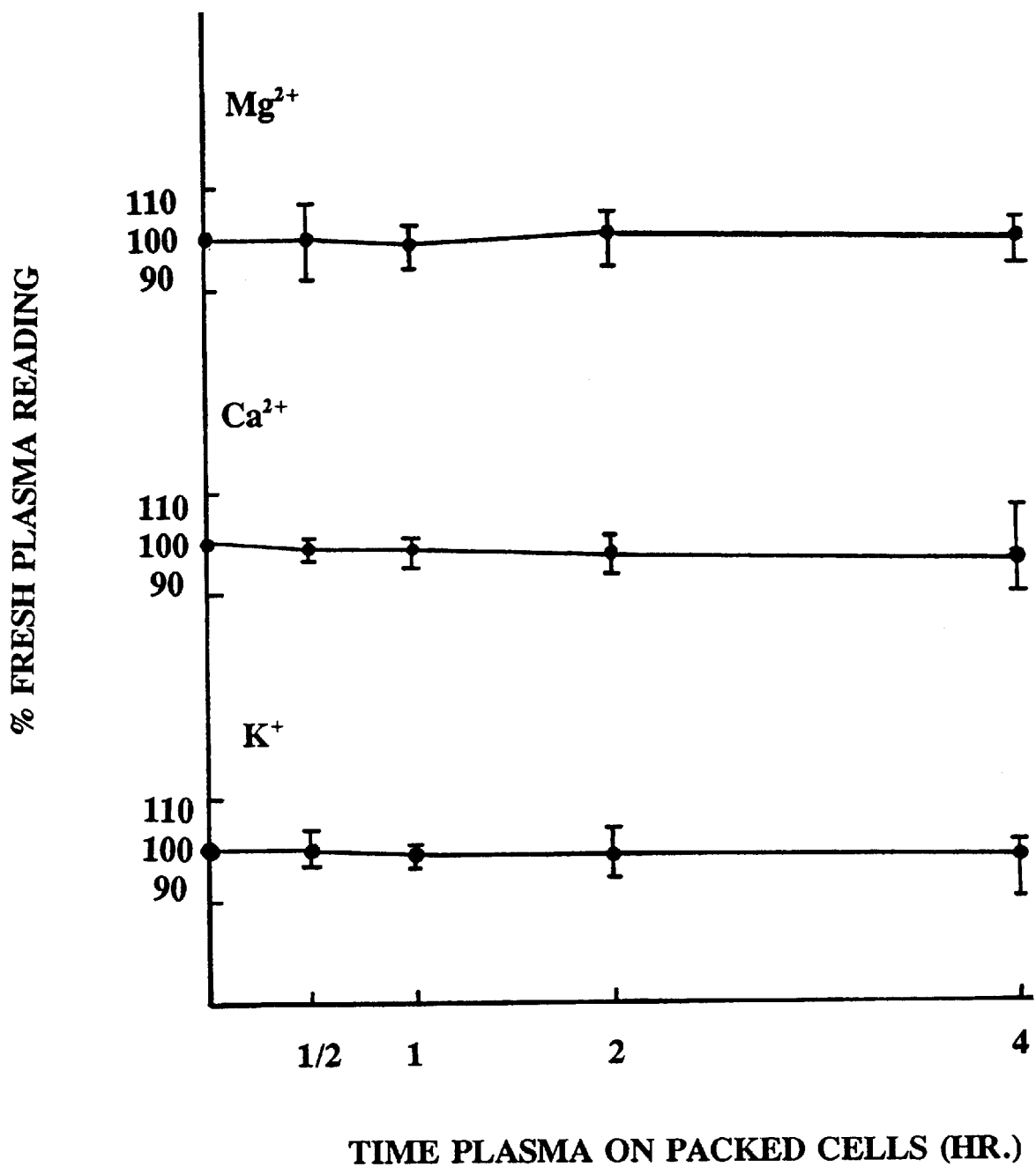
FIG. 1 shows the plasma ionized $Mg^{2+}$ concentrations from the whole blood which was spun to pack the formed elements such as erythrocytes, and stored anaerobically for 4 hours at room temperature. It shows that whole blood can be stored for at least 4 hours if stored anaerobically without affecting the ionized $Mg^{2+}$ values as compared to an ionized $Mg^{2+}$ concentration for fresh plasma.

The present invention relates to a method of treating headache comprises administration of a sufficient amount of a magnesium salt or mixture of magnesium salts to prevent or eliminate a headache. A sufficient amount of a magnesium salt or mixture of magnesium salts is that amount which prevents development of a headache or alleviates or lessens the severity of the headache anil symptoms associated with a headache, such as pain, aura, photophobia, phonophobia, and the like as well as neurological deficits such as hemisensory loss, vertigo, or visual disturbances and the like. In addition to preventing or alleviating or lessening the symptoms of the headache, the amount of magnesium salt or mixture of magnesium salts is sufficient to raise the ionized magnesium concentration in the serum to within a normal range of serum ionized magnesium as determined using an ion-selective electrode as described herein. The sufficiency of the amount of magnesium salt provided to the patient may also be determined by $^{31}P$ NMR spectroscopy of ionized magnesium concentrations in the brain of the patient [Altura, et al. *Magnes. Trace Elem.*, 10(2–4); 122–35, 1991–92]. The amount of magnesium salt should be an amount sufficient to raise the ionized magnesium concentrations in the brain.

The amount of the magnesium salt or mixture thereof for treatment or prevention of headache is about 500 mg to about 5 gms, preferably 1 gm to about 2 gms. In one embodiment the magnesium salt is provided in a dose of about 1-to-about 3 grams, preferably about 1 gram.

The above concentration of salt or mixture thereof is sufficient to provide to the patient an elemental concentration of magnesium of about 200 mg to about 400 mg.

In one embodiment the magnesium salt is in the form of magnesium sulfate ($MgSO_4$). Other magnesium salts that are useful in the present invention include but are not limited to $MgCl_2$, $MgCl_2.6H_2O$, $MgSO_4.7H_2O$, and other magnesium salts that are highly water soluble, highly bioavailable and safe for human use. The magnesium salt is provided as a pharmaceutical composition in a pharmaceutically acceptable carrier. The pharmaceutical composition for oral administration of the magnesium salt or mixture thereof is provided only as an aqueous solution, not in tablet form. The carrier for the oral pharmaceutical composition is preferably water, more preferably bottled water which contains little or no other anions or minerals. In addition to the magnesium salt, the pharmaceutical composition may contain one or more analgesics such as ketorolac, aspirin, acetaminophin, ibuprofin and the like. In one embodiment the composition has a magnesium salt or mixture of magnesium salts plus ketorolac which is useful for intravenous administration.

In the method of treatment of a headache intravenously, the amount or dose of a magnesium salt or mixture thereof is administered over a period of time, preferably between about two minutes to about 15 minutes, more preferably about four to about five minutes. In one embodiment the dose of magnesium salt is administered between about two to about five minutes intravenously. In other routes of administration, such as subcutaneously (S.C.), intramuscularly (I.M.), nasally and rectally, the dose is preferably provided as an immediate bolus. The dose of magnesium salt may be administered once or multiple doses of magnesium may be provided as necessary to prevent or treat headache. For oral administration, about one to about two liters of an aqueous solution of the magnesium salt is imbibed by an individual over a 24-hour period on a daily basis. The need for more than one dose of magnesium salt may monitored by symptom manifestation and by ionized magnesium and ionized $Ca^{2+}:Mg^{2+}$ ratio determinations.

The route of administration may be intravenous, S.C., I.M., nasal, rectal, oral and the like. Subcutaneous may be administered by a patient using an autoinjector device such as that used to administer sumatriptan (Dahlof, C., et al. *Arch. Neurol.* (U.S.) Vol. 51(12): 1256–61, 1994; Portugese Sumatriptan Auto-injector Study Group, *J. Int. Med. Res* (England) Vol. 22:225–35, 1994). The pharmaceutical composition and auto injector device may be provided as a kit to the individual for self treatment.

The magnesium salt of the present invention may also be administered intranasally in a manner similar to administration of sumatriptan (Salonen, R., et al. *J. Neurol.* (Germany) Vol. 241:463–9, 1994) or the like. Rectal administration may be provided by a suppository containing the magnesium salt.

The present invention encompasses a method of determining patients amenable to treatment using magnesium salts or mixtures thereof comprising determining serum levels of ionized magnesium and/or serum ionized calcium to serum ionized magnesium ratios in the individual having a headache. Patients amenable to treatment have serum ionized magnesium concentrations equal to or less than about 0.54 mmole/L, typically between about 0.44 mmole/L to about 0.53 mmole/L. Patients amenable to treatment have higher than normal serum $ICa^{2+}$:$IMg^{2+}$ ratios of about 2.25 to about 2.55.

The present invention demonstrates the clinical utility of Mg as a therapeutic regimen in alleviation of headaches. The present invention indicates a role for $IMg^{2+}$ deficiency in the etiology and development of headaches. Efficacy of a magnesium salt in the acute treatment of many patients with a variety of headaches was demonstrated. As shown by the present invention, measurement of serum $Mg^{2+}$ levels help to establish a biochemical marker for headaches.

The efficacy of administration of a magnesium salt for the treatment of patients with headaches was shown. Clinical responses were correlated with the basal serum ionized magnesium ($IMg^{2+}$) level and ionized calcium to ionized magnesium ratios. It was also determined by the present invention that patients with certain headache types exhibit low serum $IMg^{2+}$ as opposed to serum total Mg (TMg).

Patients' headache, including moderate or severe headache of any type, may benefit from treatment using a magnesium salt. Such headaches include but are not limited to migraines with or without aura, cluster headaches, chronic tension-type headaches, chronic migrainous headaches and the like.

The method of treating headaches of the present invention provides complete elimination of pain in approximately 80% of the patients within five minutes of treatment using a magnesium salt. No recurrence or worsening of pain was observed within 24 hours in greater than 50% of the patients. Patients treated with the magnesium salt of the present invention had complete elimination of migraine-associated symptoms such as photophobia and phonophobia as well as nausea. Correlation was noted between immediate and 24-hour responses with the serum $IMg^{2+}$ levels. Total Mg (TMg) levels in contrast in all headache subjects were within normal range (0.70–0.99 mM/L) Patients demonstrating no return of headache or associated symptoms within 24 hours of treatment with a magnesium salt exhibited the lowest initial basal levels of $IMg^{2+}$ prior to treatment. Non-responders exhibited significantly elevated TMg levels compared to responders. Although most subcategories of headache types investigated (i.e., migraine, cluster, chronic migrainous) exhibited low serum $IMg^{2+}$ during headache and prior to IV $MgSO_4$, the patients with cluster headaches exhibited the lowest basal levels of $IMg^{2+}$ ($p(0.01)$. All headache subjects except for the chronic tension group exhibit rather high serum $ICa^{2+}$/$IMg^{2+}$ ratios compared to controls.

The present invention relates to a method for preparing biological samples, including collection and storage conditions, prior to testing for ionized $Mg^{2+}$ concentrations which allow accurate and reproducible readings. More specifically, the invention relates to a method of collecting and maintaining biological samples under conditions which minimize or prevent exchange of gases between atmospheric air and the biological sample, preferably in which $O_2$ is substantially excluded and $pCO_2$ levels are maintained in the biological sample prior to measuring ionized $Mg^{2+}$. The preferred embodiment is a method for preparing and storing biological samples under anaerobic conditions.

The biological sample to be tested for ionized $Mg^{2+}$ is preferably a fluid or a sample that can be made fluid including but not limited to whole blood, plasma, serum, amniotic fluid, umbilical cord blood, cerebral spinal fluid, urine, gastric secretions, lacrimal secretions, peritoneal fluid, pleural fluid and the like obtained from animals, preferably mammals, most preferably humans. The fluid portion of biological tissue samples may be tested after homogenation with a tissue-homogenizer or the like if collected and maintained under conditions described herein. In the preferred embodiment, the biological sample is whole blood, plasma, serum, cerebral spinal fluid, umbilical cord blood, and amniotic fluid.

Another aspect of the invention is a method for determining ionized $Mg^{2+}$ concentrations in a biological sample, collected and maintained under conditions which minimize or prevent exchange of gases between the biological sample and atmospheric air, preferably in which $O_2$ is substantially excluded and $pCO_2$ levels are substantially maintained in the biological sample prior to measuring ionized $Mg^{2+}$, most preferably under anaerobic conditions. In one embodiment, the ionized $Mg^{2+}$ concentration is measured using an ion selective electrode with a neutral carrier based membrane. In a preferred embodiment, the ionized $Mg^{2+}$ concentration is obtained through the use of an ion selective electrode manufactured by Nova Biomedical.

Another aspect of the invention is a method for determining ionized $Ca^{2+}$:$Mg^{2+}$ ratios in a biological sample, collected and maintained under conditions which minimize or prevent exchange of gases between the biological sample and atmospheric air, preferably in which $O_2$ is substantially excluded and $pCO_2$ levels are substantially maintained in the biological sample prior to measuring ionized $Ca^{2+}$ and $Mg^{2+}$, most preferably under anaerobic conditions. In one embodiment, the ionized $Ca^{2+}$ and $Mg^{2+}$ concentrations are measured using ion selective electrodes with a neutral carrier based membrane. In a preferred embodiment, the ionized $Ca^{2+}$ and $Mg^{2+}$ concentrations are obtained through the use of an ion selective electrode manufactured by Nova Biomedical.

Ion selective electrodes based on neutral carrier membranes and the methods of their use are known in the art and are widely used as integrated devices in clinical chemistry analyzers. With their availability, a selective determination of different ions in dilute samples as well as whole blood is possible (Oesch, U. et al. Clin. Chem 32(8):1448, 1988). Neutral carrier based membranes selective for specific ions are known in the art as described by Dinten, O. et al. (Anal. Chem. 63:596–603, 1991), which is incorporated by reference. As examples, membranes composed of N,N'-diheptyl-N,N'-dimethyl-1,4-butanediamide ($C_{20}H_{40}N_2O_2$) (ETH 1117), N,N'-diheptyl-N,N'-dimethyl-aspartdiamide ($C_{20}N_{41}N_3O_2$) (ETH 2220), N,N"-octamethylenebis(N'-heptyl-N'-methyl-2-methylmalondiamide) ($C_{32}H_{62}N_4O_4$) (ETH 5214), N,N"-octamethylenebis(N',N'-dioctylmalondiamide) (ETH 5220), N',N",N"-iminodi-6,1-hexanediyldiiminotris(N-heptyl-N-methylmalonamide) ($C_{45}H_{84}NO_6$) (ETH 5282) and the like are known neutral carriers selective for $Mg^{2+}$. Some.examples of neutral carriers selective for $Ca^{2+}$ are (-)-(R,R)-N,N'-[bis(11-ethoxycarbonyl)undecyl]-N,N', 4,5-tetramethyl-3,6-dioxaoctanediamide ($C_{38}H_{72}N_2O_8$) (ETH 1001), N,N,N',N'-tetracyclohexyl-3-oxapentanediamide ($C_{28}H_{48}N_2O_8$) (ETH 129), N,N-dicyclohexyl-N',N'-dioctadecyl-3-oxapentanediamide (ETH 5234) and the like. However, until the present invention, ion selective electrodes for determining ionized magnesium concentrations were not known in the art.

The methods for determining total magnesium, ionized $Ca^{2+}$ and $Mg^{2+}$ concentrations as measured using atomic absorption spectroscopy on an ultrafiltrate are known in the art as described by Walser, M. (J. Clin. Invest. 40:723–730, 1961), D'Costa, M. (Clin. Chem. 29:519, 1983), and Zaloga, G. P. et. al. (Crit. Care Med. 15:813–816, 1987), which are incorporated by reference.

Another aspect of the invention is a method for diagnosing or prognosing disease states or conditions associated with Mg imbalances, Mg deficiencies, or $Ca^{2+}$:$Mg^{2+}$ imbalances using a method of determining ionized $Mg^{2+}$ or ionized $Ca^{2+}$:$Mg^{2+}$ ratios in a biological sample, collected and maintained under conditions which minimize or prevent exchange of gases between the biological sample and atmospheric air, preferably in which $O_2$ is substantially excluded and $pCO_2$ levels are substantially maintained in the biological sample prior to measuring ionized $Ca^{2+}$ and $Mg^{2+}$, most preferably under anaerobic conditions. Such disease states include but are not limited to cardiac diseases, cardiovascular insufficiency, cardiac arrhythmias, coronary artery spasm, those at risk for sudden death, renal disorders, lung diseases, respiratory muscle weakness, abnormal pregnancy, pre-eclampsia, eclampsia, fetal growth retardation, migraine, hypertension, idiopathic intracranial hypertension, diabetes, head trauma, premenstrual syndrome, tetany, seizures, tremor, apathy, depression, hypokalemia and hypocalcemia. The $Mg^{2+}$ values of the patient are compared to normal ionized $Mg^{2+}$ values for biological samples. In one embodiment, the normal ionized $Mg^{2+}$ concentration in a normal adult is approximately 0.53 to 0.67 mM, most preferably about 0.58–0.60 mM for the biological sample of whole blood, serum, and plasma. In another embodiment, the normal ionized $Mg^{2+}$ concentration is approximately 1.10–1.23 more preferably 1.12–1.19 mM for the biological sample of cerebral spinal fluid.

A further aspect of the invention is a method of maintaining normal ionized $Mg^{2+}$ concentrations in a patient in need of such maintenance by administering ionized $Mg^{2+}$ in a concentration sufficient to maintain levels of ionized $Mg^{2+}$ in biological samples within a normal range of ionized $Mg^{2+}$. In one embodiment, the normal ionized $Mg^{2+}$ concentration in a normal adult is approximately 0.53 to 0.67 mM, most preferably about 0.58–0.60 mM for the biological sample of whole blood, serum, and plasma. In another embodiment, the normal ionized $Mg^{2+}$ concentration is approximately 1.10–1.23 more preferably 1.12–1.19 mM for the biological sample of cerebral spinal fluid. Another aspect of the invention is a method to attain or maintain normal ionized $Mg^{2+}$ or $Ca^{2+}$ and ionized $Mg^{2+}$ concentrations in a patient in need of such maintenance by administering $Ca^{2+}$ and $Mg^{2+}$ in a concentration sufficient to maintain a normal physiological molar ratio of ionized $Ca^{2+}$/ionized $Mg^{2+}$ in the blood of about 1:1 to 2.5:1, more preferably about 1.5:1, and most preferably about 2:1, or to maintain a normal physiological molar ratio of ionized $Ca^{2+}$/ionized $Mg^{2+}$ in the cerebral spinal fluid of about 0.90:1 to about 1.15:1, more preferably 0.92:1 to about 1.1:1, most preferably about 1:1.

Another aspect of the invention is a method to attain or maintain normal ionized $Mg^{2+}$ or normal ionized $Ca^{2+}$ and $Mg^{2+}$ concentrations in a neonate, infant, and child in need of such maintenance by administering $Mg^{2+}$ alone or in combination with $Ca^{2+}$ in a concentration sufficient to maintain a normal physiological molar ratio ionized $Ca^{2+}$/ionized $Mg^{2+}$ in the blood of about 1.9:1 to about 2.6:1, more preferably about 2.3:1 to about 2.5:1.

An additional aspect of the invention is a composition for use in preventing or treating magnesium imbalances, magnesium deficiencies or $Ca^{2+}$:$Mg^{2+}$ imbalances, the composition is composed of bioavailable magnesium alone or in combination with bioavailable calcium in an effective concentration. The concentration of calcium and magnesium is a concentration that provides to arn individual a normal physiological molar ratio of ionized calcium to ionized magnesium in the blood of about 1:1 to 2.5:1, more preferably about 1.5:1, and most preferably about 2:1, or to maintain a normal physiological molar ratio of ionized $Ca^{2+}$/ionized $Mg^{2+}$ in the cerebral spinal fluid of about 0.90:1 to about 1.15:1, more preferably 0.92:1 to about 1.1:1, most preferably about 1:1. In another embodiment the concentration of calcium and magnesium is a concentration that provides to a neonate, infant and child a normal physiological molar ratio of ionized calcium to ionized magnesium in the blood of about 1.9:1 to about 2.6:1, more preferably about 2.3:1 to about 2.5:1. The composition is useful in treating individuals with the following disease states such as cardiac diseases, hypertension, idiopathic intracranial hypertension, diabetes, lung diseases, abnormal pregnancy, preeclampsia, eclampsia, head trauma, fetal growth retardation or other diseases associated with magnesium deficiencies or an imbalance of ionized $Ca^{2+}$/ionized $Mg^{2+}$ ratios in the whole blood, plasma, serum, cerebral spinal fluid or the like.

The use of the composition is not limited to individuals with the aforementioned diseases but may also be used in healthy individual for maintaining proper ionized magnesium or ionized calcium/ionized magnesium concentrations. Such maintenance is useful in preventing magnesium imbalances, $Ca^{2+}$/$Mg^{2+}$ imbalances, or magnesium deficiencies and in turn is useful in preventing magnesium-associated disease states.

The composition may be taken alone as a therapeutic agent in a pharmaceutically acceptable carrier or a mineral supplement, or the composition may be added to supplement other ingredients such as, but not limited to, vitamin formulations, vitamin and mineral formulations, and foodstuffs. Such food stuffs include solids and liquids. In one embodiment the composition is added to infant formulas.

EXAMPLE I

Sample Collection

In order to obtain precise and reproducible determinations of ionized $Mg^{2+}$ with the ISE, blood samples were collected under conditions that minimize or prevent exchange of atmospheric gases with those of the sample, most preferably under anaerobic conditions into a tube with the air evacuated, such as a Vacutainer™ tube, or other tube or syringe substantially free of atmospheric gases, especially $O_2$. The tube or syringe may contain heparin (<75 u/ml, more preferably <50/ml, most preferably <20 u/ml). After collection of the biological sample, the samples are placed in and kept under conditions that minimize or prevent exchange of atmospheric gases with those of the sample, mosit preferably under anaerobic conditions (FIG. 1).

EXAMPLE II

Sample Processing

To process clotted blood or plasma (heparinized blood), the samples were maintained under conditions that minimize or prevent exchange of gases between atmospheric air and the biological sample, preferably anaerobic conditions in tubes sealed with rubber stoppers. Parafilm or plastic and glass tops cannot be utilzed as this allows for air to enter the sample. If samples (ie., whole blood, serum or plasma) were analyzed (or frozen) more than 30 min after blood draw for processing of serum or plasma, the sealed tubes were placed in a standard clinical or laboratory centrifuge and centrifuged at 3,000–4,000 rpm for 15–20 minutes. After this time, the sera or plasma was carefully removed from the packed cells by inserting a sterilized needle attached to either a plastic syringe (for sera) or a lightly heparinized (<75 u/ml, more preferably <50 u/ml, most preferably <20 u/ml) glass syringe (for plasma) or a similar device.

EXAMPLE III

Sample Storage

Figure 2:
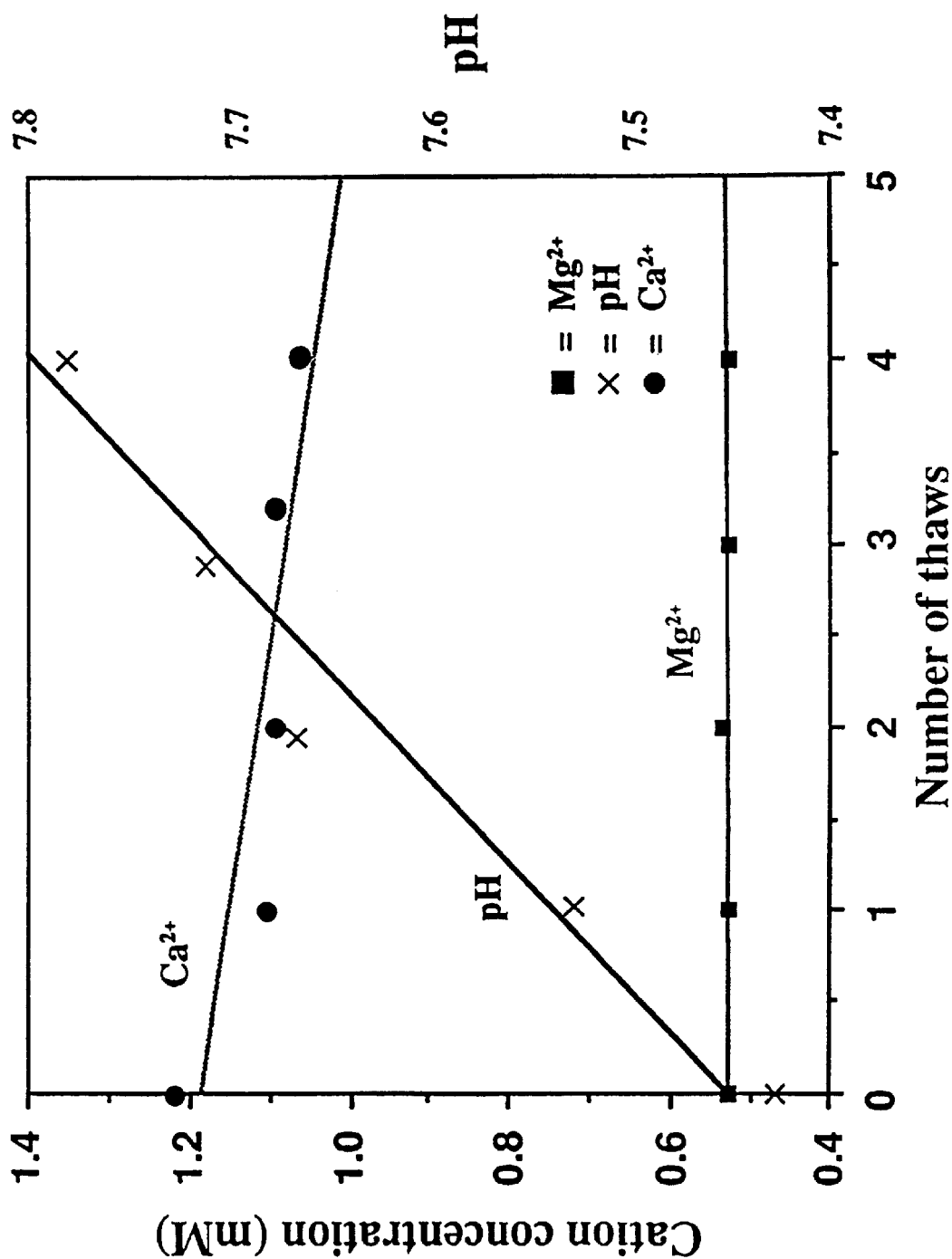
FIG. 2 shows that freeze-thawing samples has virally no effect on the ionized $Mg^{2+}$ values for samples stored under anaerobic conditions. In contrast, ionized $Ca^{2+}$ values decline with repeated freeze-thawing of the sample.

The anaerobically maintained samples were either processed with the ISE within six hours or the plasma or serum carefully expelled into a tube with the air evacuated or other tube or syringe substantially free of atmospheric air, especially $O_2$, most preferably anaerobic, with or without heparin, and frozen at −10° C. Unlike ionized $Ca^{2+}$, ionized $Mg^{2+}$ levels were stable during numerous subsequent freeze-thaw procedures, provided the bloods were drawn and processed under anaerobic conditions as described above (see FIG. 2, Table 1). Under conditions where parafilm coverings were used, pH and $pCO_2$ changes occurred causing erratic and erroneous ionized $Mg^{2+}$ values.

TABLE 1

Influence of Freeze–Thawing with Parafilm Covering on Plasma pH and Ionized Free $Mg^{2+}$ Obtained with an Ion Selective Electrode

| Para- | Day of Examination | | | |
|---|---|---|---|---|
| meter | 1 | 2 | 3 | 12 |
| pH | 7.435 ± 0.010 | 7.685 ± 0.044 | 7.897 ± 0.056 | 8.26 ± 0.070 |
| $Mg^{2+}$ (mM) | 0.64 ± 0.035 | 0.65 ± 0.04 | 0.60 ± 0.029 | 0.53 ± 0.036 |

Using the method of the present invention, plasma and serum samples were frozen for up to two weeks at −10° C. without affecting the ionized $Mg^{2+}$ values. Whole blood samples were maintained under anaerobic conditions at room temperature for up to six hours after blood draws prior to ionized $Mg^{2+}$ determinations. These and other experiments clearly indicated that as the biological samples such as blood, sera or plasma became exposed to air, they loose $CO_2$, and as a consequence the pH became alkaline. This adversely affected the ionized free $Mg^{2+}$ values resulting in erroneous readings. This is completely obviated with proper handling as describe for this invention.

EXAMPLE IV

Sample Preparation for Precision, Specificity and Interferant Studies

Male and female subjects that had no electrolyte abnormalities, ages ranging from 19–83 years, were used for the reference range study.

Whole blood and plasma samples were collected using a needle attached to heparinized Vacutainer tubes; serum from-red top Vacutainer tubes. All blood samples were collected and maintained under anaerobic conditions and processed within 1–2 hours of collection. Ultrafilterable Mg was obtained using an Amicon micropartition system (3,000 MW cutoff) after centrifugation of the plasra or serum at 1,500 to 2,000 RCF (g) for 20 minutes. A 3,000 MW cutoff was utilized in order to retain small molecular wt peptides. However, when normal sera from six volunteers were processed using a 30,000 MW cutoff virtually identical results were obtained.

Precision (within run, day-to-day) was determined on three levels of aqueous control solutions obtained from NOVA Biomedical containing 115,135 and 155 mM $Na^+$; 2.0, 3.75, and 5.75 mM $K^+$; 0.50, 1.00 and 1.50 mM $Ca^{2+}$; and 0.30, 0.50, and 1.00 mM $Mg^{2+}$ at pH values of 7.15, 7.35, and 7.58, respectively.

Aqueous solutions of $MgCl_2$ were examined for the linearity study and aqueous solutions of various cations ($Ca^{2+}$, $K^+$, $Na^+$, $H^+$, $NH_4^+$, $Fe^{3+}$, $Cu^{2+}$, $Zn^{2+}$, $Cd^{2+}$, $Hg^{2+}$, and $Pb^{2+}$) were examined over pathophysiologic concentration ranges for potential interference to the new $Mg^{2+}$ electrode. The concentrations of potentially interfering cations were chosen based on the following observations: the upper limit of the reference range (ULRR) for $NH_4^+$ is <100 μM; the toxic range for $Cd^{2+}$ has been listed up to 27 μM; concentrations for $Ca^{2+}$ rarely exceed 2.0 mM; the ULRR for $Cu^{2+}$ is <30 μM; for $Fe^{2+}$ <50 μM; for $Pb^{2+}$ <2 μM; for $Hg^{2+}$ <0.25 μM; and for $Zn^{2+}$ 23 μM. $K^+$ above 10 mM and $Na^+$ above 175 mM are rarely seen in plasma. Ligand binding studies were also carried out in aqueous solutions containing pathophysiological concentrations of heparin, lactate, acetate, phosphate, bicarbonate and sulfate.

Albumin/pH studies employed bovine serum albumin (Sigma Chem. Co., St. Louis, Mo.) that was treated with an anion-exchange resin (Exchange Resin AG50W-48, Bio-Rad Richmond, Calif.) resulting in a solution that had 6 g albumin/dl and unmeasurable TMg (<0.04 mM, as assessed by atomic absorption spectrophotometry). This solution was lyophilized followed by gravimetric addition of lyophylate to aliquots of an aqueous solution containing a fixed amount of Mg.

Spiking experiments with plasma (pH 7.6–7.7) and whole blood (pH 7.40–7.44) were also performed with addition of various concentrations of mostly $MgCl_2$ and some with $MgSO_4 \bullet 7H_2O$ (Biological Grades, ACS certified, Fisher Scientific, New Jersey) at room temperature. Electrode analyses for $IMg^{2+}$ results, were performed immediately after being well-mixed, and after 5 and 10 min; results were identical at all three time intervals.

All chemicals used to make up the aqueous solutions were of high purity (biological, ACS certified grades) and obtained form Fisher Scientific Co., and Sigma Chemical Co.

For most aqueous solutions, a 5 mM HEPES buffered-physiologic salt solution (in Mm/L) (120–140 NaCl; 4–5 KCl; 1 $CaCl_2$) was used. In some cases, due to increased acidity, caused by certain ligands, 10 mM HEPES was added to the latter instead of 5 mM HEPES. In the case of the pH studies, modified KREBS-Ringer bicarbonate buffered physiological salt solutions were used (in mM/L) (118 mM NaCl; 4.7 KCl; 1.2 $KH_2PO_4$; 1.0 $CaCl_2$; 25 $NaHCO_3$) gassed with a 5% $CO_2$–95% $O_2$ mixture.

A NOVA Stat Profile 8 (SP8) Analyzer (NOVA Biomedical, Waltham, Mass.) containing the specially-designed $Mg^{2+}$ electrode along with electrodes for $Ca^{2+}$, $Na^+$, $K^+$, and pH, and, where appropriate, hematocrit, was used for these studies.

The electrode is calibrated by using two aqueous solutions containing different concentrations of $MgCl_2$ in the presence of known pH and concentrations of $Na^+$, $K^+$, and $Ca^{2+}$. The values assigned to these solutions are determined gravimetrically. The electrical signal from the $Mg^{2+}$ electrode is mathematically adjusted by the signal from the $Ca^{2+}$ electrode to provide the resulting $Mg^{2+}$ concentration. All electrode measurements can be made on a 250 μl sample (whole blood, plasma or serum) within 90–120 seconds. The SP8 is equipped with its own on-board calibrators.

Total magnesium values are obtained on a Perkin-Elmer Model Zeeman 5000 atomic absorption spectrophotometer (AAS), utilizing 1% $LaCl_3$ (Fisher Scientific) to prevent any interferences.

Data were evaluated for statistical significance using means±S.E.M., unpaired t-tests, ANOVA, method of least squares for regression analyses and correlation coefficients, where appropriate. A p value less than 0.05 was considered significant.

EXAMPLE V

Figure 3:
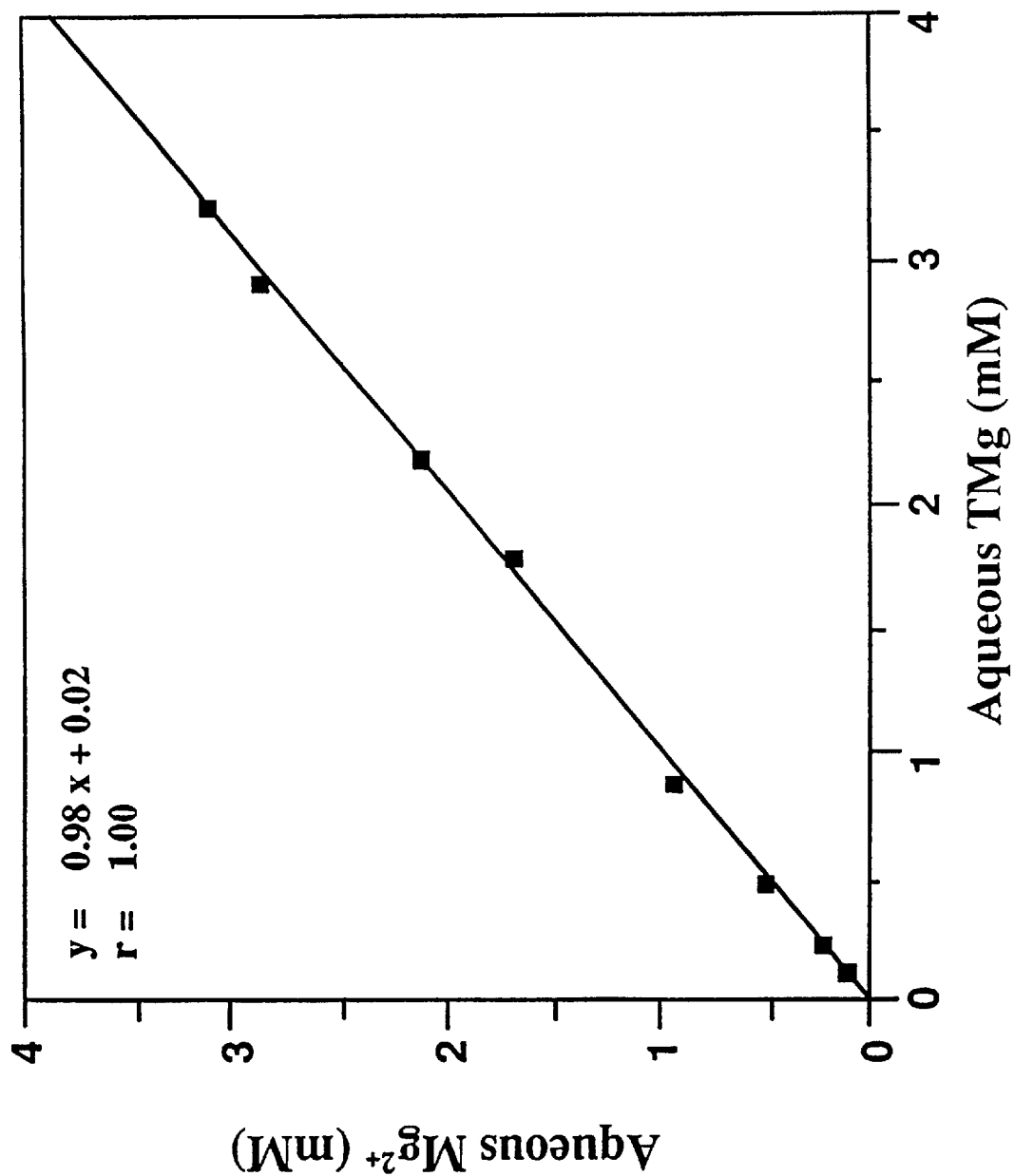
FIG. 3 aqueous $Mg^{2+}$ vs. aqueous TMg. Correlation of ionized magnesium ($Mg^{2+}$) values by ion selective electrode (ISE) with total magnesium (TMg) values by atomic absorption spectroscopy taken on unbuffered aqueous solutions of $MgCl_2$.

Determination of Magnesium in Aqueous Solutions: ISE Comparison to Atomic Absorption FIG. 3 illustrates that the $Mg^{2+}$ electrode quantifies Mg comparably to atomic absorption spectroscopy in aqueous solution. In the absence of binding ligands, it would be predicted that the values from the two technologies would be identical. Results from these measurements were linear over the entire 0.1 to 3.0 mM $Mg^{2+}$ range studied.

EXAMPLE VI

Precision and Reproducibility

Using the ISE on three levels of aqueous $Mg^{2+}$ controls, mean values over a range of 0.3 to 1.0 mM are within 94.6 and 99.2% of their targets. The linearity of the ISE (0.1–3.0 mM) in aqueous solution and human plasma and serum ranges between 92.0 and 99.3%.

EXAMPLE VII

Effects of Albumin and pH on Measured $IMg^{2+}$ Levels

The effect of protein on measured $IMg^{2+}$ levels were strongly affected by the pH of the medium. Results in Table 2 show that, in unbuffered solutions, addition of albumin up to a final concentration of 150 g/l produces a moderate decline in measured $IMg^{2+}$ values. The observed decline in pH of the medium upon addition of albumin is expected since the protein has a acidic isoelectric point. If, however, the pH of the solution is carefully ally by addition of NaOH, measured $IMg^{2+}$ values decline by up to 75%, indicating that the exposure of anionic groups on albumin promotes the binding of $Mg^{2+}$.

TABLE 2

Adding Albumin to an Aqueous Mg Solution Followed by Alkalinization

| Albumin added (g/L) | pH | $Mg^{2+}$ (mM) | $Mg^{2+}$ (mM After adjusting pH to 8.24 ± 0.03) |
|---|---|---|---|
| 0 | 7.45 | 0.49 | |
| 30 | 7.02 | 0.44 | 0.39 |
| 60 | 6.67 | 0.41 | — |
| 90 | 6.37 | 0.40 | 0.20 |
| 120 | 6.15 | 0.40 | 0.17 |
| 150 | 5.98 | 0.43 | 0.13 |

Figure 4:
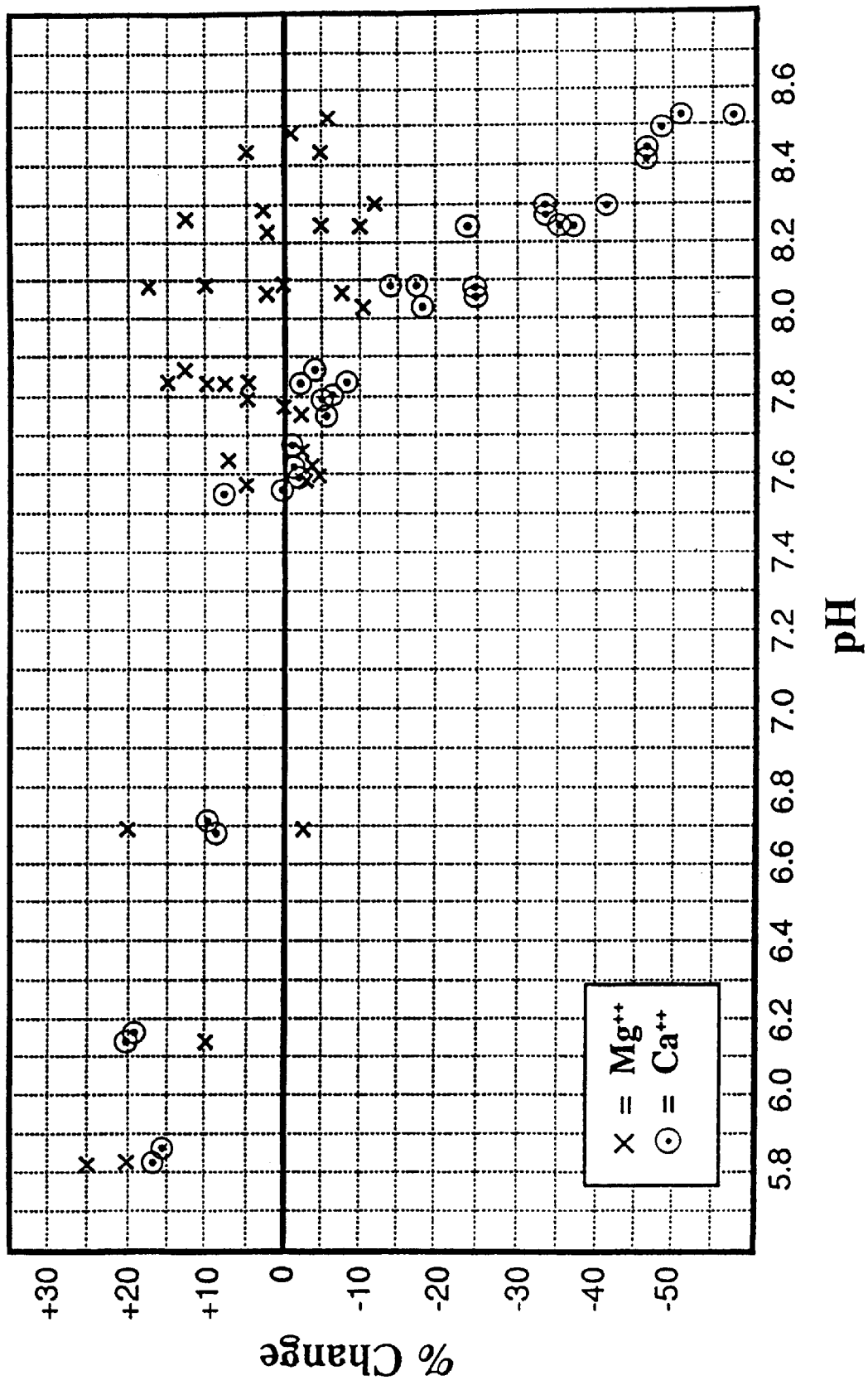
FIG. 4 $Mg^{2+}$ and $Ca^{2+}$ changes in aqueous buffered solutions with changes in pH as determined by an ISE.

To differentiate a possible direct effect on pH on the performance of the electrode, measurements over a similar range of pH values (buffered by phosphate and/or bicarbonate) were performed in the absence of albumin. Results in FIG. 4 show that $IMg^{2+}$ measurements are minimally affected over the pH ramge examined (6.2 to 8.5). Only at the lower pH values were measurements of $IMg^{2+}$ levels affected (10–20%). These studies, thus, show that over the pH ranges examined, pH per se does not significantly influence the measured $IMg^{2+}$ values. $H^+$ clearly affects $ICa^{2+}$ much more than $IMg^{2+}$, causing an apparent 140% decrease in $ICa^{2+}$ over the pH range of 6.3 to 8.3. This is likely due to the precipitation of calcium compounds.

EXAMPLE VIII

Effects of Common Cations and Heavy Metal Ions on $IMg^{2+}$ Values

Virtually no interference was noted from pathophysiologic concentrations of any of the cations added to an aqueous solution containing $Mg^{2+}$ with the possible exception of $Zn^{2+}$ (Table 3). Adding calcium salts to serum creased in the $IMg^{2+}$ (~0.1 mM $Mg^{2+}$ for a 1.0 mM increase in $Ca^{2+}$), but a much smaller increase was seen when calcium was added to an aqueous solution containing $Mg^{2+}$ (~0.01–0.04 mM $Mg^{2+}$ for a 1.77 mM increase of $Ca^{2+}$). The change in plasma $IMg^{2+}$ is likely the result of added $Ca^{2+}$ competing for binding sites held by $Mg^{2+}$ in the plasma. The concentration of $NH_4^+$ and heavy metal ions represent the upper limit.of their reference range, except for $Cd^{2+}$, whose concentration was toxic.

TABLE 3

Influence of Common Cations and Heavy Metal Ions on the $Mg^{2+}$ Determined by ISE

| Cation | Final Cation conc. in plasma | $Mg^{2+}$ (mM) in plasma | Final Cation conc. in water | $Mg^{2+}$ (mM) in the aqueous solution Soln. 1 | Soln. 2 |
|---|---|---|---|---|---|
| $NH_4^+$ | | | 0 mM | 0 | |
| | | | 1 | 1 | |
| $Cd^{2+}$ | 0 μM | 1.25 ± 0.050[a] | | | |
| | 57 | 1.24 ± 0.051 | | | |
| $Ca^{2+}$ | 0.75 mM | 1.02 ± 0.003 | 1.02–1.32 mM | 0.50 | 0.56 |
| | 1.50 | 1.01 ± 0.010 | 1.46–148 | 0.50 | 0.57 |
| | 1.90 | 1.07 ± 0.011 | 1.87–2.79 | 0.51 | 0.58–0.60 |
| $Cu^{2+}$ | 0 μM | 0.94 ± 0.025 | | | |
| | 24 | 0.94 ± 0.010 | | | |
| $Fe^{3+}$ | 0 μM | 1.25 ± 0.050 | | | |
| | 28.6 | 1.23 ± 0.020 | | | |
| $Pb^{2+}$ | | | 0 μM | | 0.50 |
| | | | 1.93 | | 0.51 |
| $Hg^{2+}$ | 0 μM | 0.88 ± 0.015 | | | |
| | 0.10 | 0.88 ± 0.015 | | | |
| $K^+$ | 4.18 mM | 1.02 ± 0.005 | 0 mM | 0 | |
| | 10.00 | 0.97 ± 0.005 | 5 | 0 | |
| $Na^+$ | 145 mM | 1.01 ± 0.00 | 0 mM | 0 | |
| | 175 | 1.02 ± 0.003 | 75 | 0.01 | |
| $Zn^{2+}$ | 0 μM | 0.91 ± 0.020 | | | |
| | 10 | 0.91 ± 0.019 | | | |
| | 18 | 0.99 ± 0.050 | | | |
| | in serum (μM) | | | | |
| | 0 | 0.57 | | | |
| | 25 | 0.61 | | | |

[a]Values are means ± S.E.M.

EXAMPLE IX

Small Ligand Binding to $Mg^{2+}$

It appears that plasma samples having a hepann concentration of 20 units/ml or less will produce less than a 4% error for the $IMg^{2+}$ determination (Table 4). Several small ligands (e.g., acetate, bicarbonate, citrate, lactate, phosphate, sulfate), on the other hand, may bind significant amounts of $Mg^{2+}$, suggesting that the $IMg^{2+}$/TMg ratio could vary within a patient over time, in an acute-care setting depending on the solutions the patient is receiving.

TABLE 4

Performance of $Mg^{2+}$ ISE in Presence of Various Ligands in Aqueous Solution

| Ligand | Concentration | Average $[Mg^{2+}]$ Location 1 | Location 2 | Average % change in $[Mg^{2+}]$ |
|---|---|---|---|---|
| acetate | 0 mM | 1.04 | 2.22 | 1.03 |
| | 0.5 | 0.99 | 2.20 | 1.03 | −2 |
| | 20.0 | 0.92 | 1.86 | 0.95 | −12 |
| bicarbonate | 0 mM | 1.09 | 2.09 | 1.03 |
| | 10 | 1.01 | 1.96 | 1.07 | −3 |
| | 40 | 0.94 | 1.85 | 0.99 | −10 |

TABLE 4-continued

Performance of $Mg^{2+}$ ISE in Presence of Various Ligands in Aqueous Solution

| Ligand | Concentration | Average [$Mg^{2+}$] Location 1 | Location 2 | | Average % change in [$Mg^{2+}$] |
|---|---|---|---|---|---|
| citrate | 0 mM | 1.18 | 2.19 | | |
| | 0.5 | 0.88 | 1.80 | | −22 |
| | 20.0 | 0.08 | 0.17 | | −94 |
| heparin | 0.0 U/ml | 1.05 | 1.96 | 1.03 | |
| | 10 | | | 1.07 | +4 |
| | 20 | 0.97 | 1.94 | 1.01 | −4 |
| | 50 | 0.90 | 1.89 | | −9 |
| | 100 | 0.83 | 1.71 | 0.95 | −14 |
| | 500 | 0.50 | 1.07 | | −49 |
| lactate | 0 mM | 0.97 | 2.19 | | |
| | 0.5 | 0.92 | 1.98 | | −8 |
| | 20.0 | 0.76 | 1.64 | | −24 |
| phosphate | 0 mM | 1.06 | 2.02 | 1.03 | |
| | 1 | 1.06 | 1.90 | 1.03 | −2 |
| | 2 | 0.95 | 1.69 | | −13 |
| | 5 | | | 0.81 | −21 |
| sulfate | 0 mM | 1.05 | 2.02 | 1.03 | |
| | 0.1 | 1.04 | 1.98 | 1.03 | −1 |
| | 1.0 | 0.99 | 2.00 | 1.01 | −3 |
| | 10.0 | 0.93 | 1.80 | | −11 |

EXAMPLE X

Reference Ranges

Assessment of ionized $Mg^{2+}$ in whole blood, plasma and serum with the ISE indicate that ionized $Mg^{2+}$ is held within an extremely narrow range (0.53–0.67 mM, mean= 0.58±0.0065, n=60) when compared to total Mg (0.70–0.96 mM, mean=0.81 mM±0.0084) or ionized $Ca^{2+}$ (1.09–1.30 mM). This narrow range for ionized $Mg^{2+}$ has not previously been reported. These data were derived from approximately 60 normal healthy human subjects. The $IMg^{2+}$/TMg ratio in this group ranged from 61–85% with a mean of 71.6±0.58%. The mean value for ionized $Mg^{2+}$ is approximately one-half of what it is for ionized $Ca^{2+}$ and thus, represents a $ICa^{2+}/IMg^{2+}$ ratio in human blood (plasma or serum) of about 2.0. Such a narrow range for ionized $Mg^{2+}$ obtained with the ISE suggested that slight changes in the normal ionized $Mg^{2+}$ range could be diagnostic and prognostic for numerous pathophysiologic states and disease conditions in animals and human subjects (Altura et al. Clinical Res., in press; Handwerker, S. et al. Magnesium and Trace. Elements, in press; Altura et al. Magnesium and Trace Elements, in press).

EXAMPLE XI

Comparison of Mg Levels in Whole Blood, Plasma, Serum and Their Ultrafiltrates A comparison of the measured levels of TMg and $IMg^{2+}$ in whole blood, plasma and serum are shown in Table 5. All values shown are based on analysis of samples collected from healthy volunteers, with the exception of serum samples having an n value of 237, which included samples collected from patients undergoing cardiac surgery.

TABLE 5

Regression Analysis of Serum, Plasma and Whole Blood Ionized $Mg^{2+}$ and Total Mg

| Regression of y on x | n | r | Slope | Intercept | y Mean | y SD | x Mean | x SD |
|---|---|---|---|---|---|---|---|---|
| $STMg^a$ on $PTMg^a$ | 21 | 0.81 | 0.63 | 0.30 | 0.83 | 0.06 | 0.84 | 0.08 |
| $SMg^{2+b}$ on $PTMg^{2+b}$ | 21 | 0.93 | 0.89 | 0.08 | 0.59 | 0.05 | 0.58 | 0.06 |
| $PMg^{2+b}$ on $PTMg^a$ | 74 | 0.80 | 0.55 | 0.13 | 0.56 | 0.06 | 0.78 | 0.08 |
| $SMg^{2+b}$ on $STMg^a$ | 237 | 0.88 | 0.71 | 0.01 | 0.74 | 0.20 | 1.039 | 0.25 |
| $WBMg^{2+b}$ on $PMg^{2+}$ | 18 | 0.79 | 1.02 | −0.02 | 0.57 | 0.05 | 0.57 | 0.06 |

STMg = serum total Mg
PTMg = plasma total Mg
$SMg^{2+}$ = serum ionized Mg
$PMg^{2+}$ = plasma ionized Mg
$WBMg^{2+}$ = whole blood ionized Mg
[a]Assessed by atomic absorption spectroscopy
[b]Assessed by ISE for $Mg^{2+}$ The highest correlation obtained (0.93) was for comparisons of $IMg^{2+}$ in plasma and serum samples. Interestingly, a significantly (p=0.02) lower correlation (r=0.79) was observed when a similar comparison was made between $IMg^{2+}$ levels in plasma vs. whole blood. The greater variance observed may suggest that a slight redistribution of bound $Mg^{2+}$ occurs upon removal of formed blood elements. The lower values of r, seen for comparisons of TMg to $IMg^{2+}$ in serum and plasma samples indicates that a range of $IMG^{2+}$ values exist for a given level of TMg. This is clearly seen in FIG. 5 which is a plot of serum TMg vs. $IMg^{2+}$ values shown in Table 5. A greater range of $IMg^{2+}$ values are seen in this plot, as many of the samples were from patients in whom cardioplegia was induced using $Mg^{2+}$-supplemented solutions.

Results of measurements of $IMg^{2+}$ and TMg performed on ultrafiltrates of serum and plasma and neat-samples are shown in Table 6. Plasma samples are collected from healthy volunteers, whereas serun-L samples also included ones from the cardiac patients. A comparison of mean values for TMg demonstrates that plasma and serum protein-free filtrates have TMg levels of 65% (0.55/0.84×100) and 71% (0.66/0.93×100), respectively, of these measured in the neat-samples. These values are similar to $IMg^{2+}$ levels measured in the neat-samples. Subsequent measurements on ultrafiltrates with the ISE, however, yielded values that were only 79% (0.45/0.57×100) and 85% (0.64/0.75×100) respectively, of the filtered TMg levels in these samples. These lower levels indicate that low molecular weight compounds are present which can chelate $Mg^{2+}$, rendering this fraction insensitive to the ISE. The size of this fraction, however, is likely somewhat overestimated by these measurements as the pH of the ultrafiltrates was always greater than the starting pH value of the unfiltered samples by 0.6–1.1 units, thereby reducing competition between $H^+$ and $Mg^{2+}$ for binding to these agents.

Figure 5:
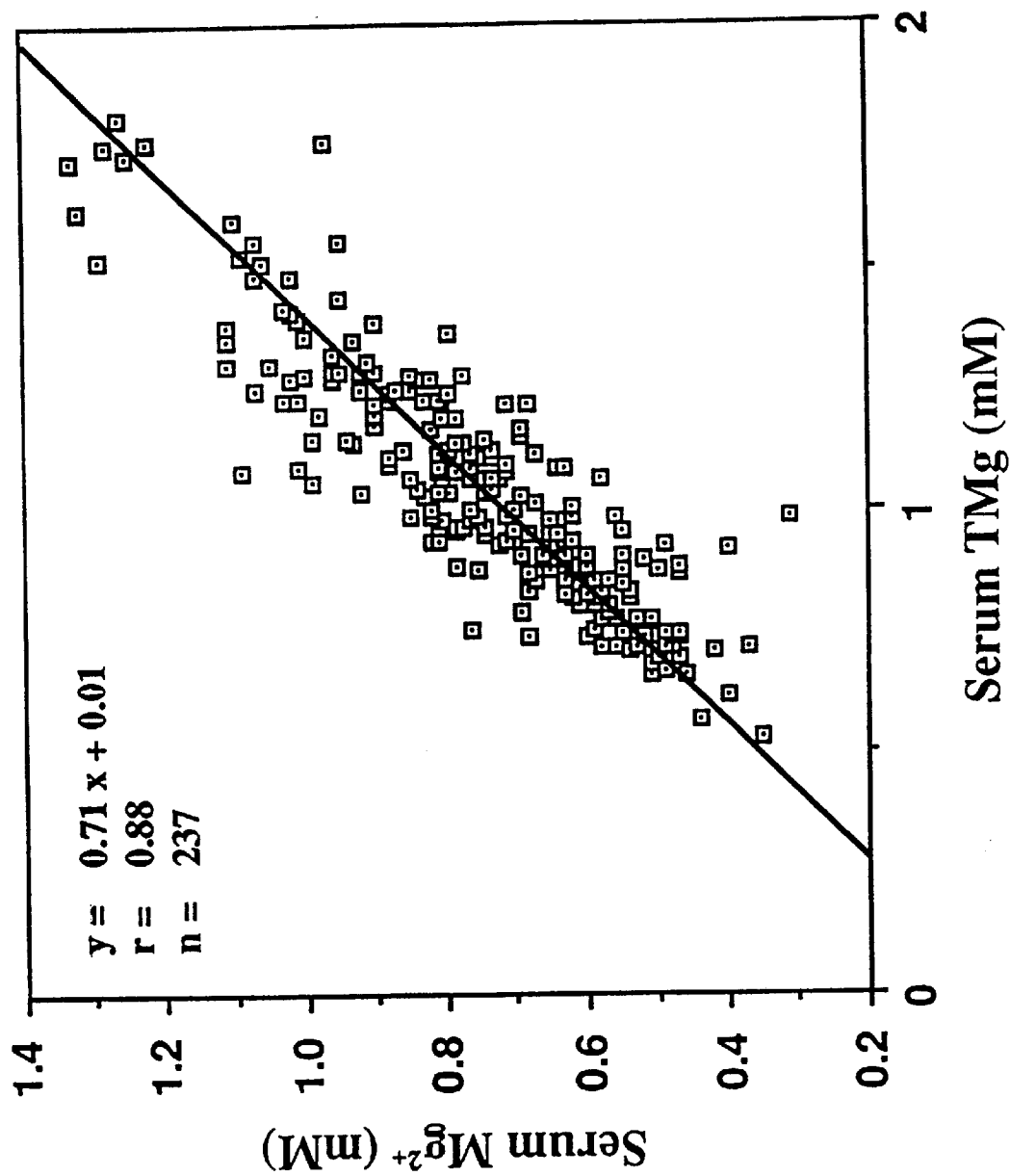
FIG. 5 shows the correlation between serum $Mg^{2+}$ values as measured on ultrafiltrate $Mg^{2+}$ by atomic absorption vs. ionized $Mg^{2+}$ values determined by an ISE. There was a correlation of R=0.88.

The increase in scatter between $TMg^{2+}$ and $IMg^{2+}$ going from FIG. 3 (aqueous solutions) to FIG. 5 (patients samples) results from differences in Mg binding to ligands and proteins from sample to sample. However, the ratio of $IMg^{2+}/TMg$ was remarkably similar, averaged across 74 plasma samples and across 237 serum samples; 71% in both cases (Table 5) even though the $IMg^{2+}/TMg$ ratio for individual patients different significantly from the average. This suggests that 29% of the TMg was typically bound to small anions and/or proteins in the "normal" and the CPB patient populations included in this study. These results suggest less binding of Mg to protein then has been described in the literature; 33–34% protein-bound by Speich et al. (*Clin. Chem.* 1981.27:246–248) and 32% protein-bound by Krofl et al. (*Clin. Chem.* 1985.31:244–246).

The present ultrafiltration studies raise questions in terms of what Mg fraction(s), or portions thereof, the ultrafiltrate actually represents. It has long been thought that the ultrafiltrate is really the plasma (or serum) minus only large molecular weight proteins with their bound Mg (Aikawa, J. K., *Magnesium. Its Biological Significance* Boca Raton: CRC Press, 1981; Walser, M. 1967. *Rev. Physiol. Biochem. Exp. Pharmacol* 59:185–341; Elin, R. J. *Clin. Chem.* 1987.33:1965–1970). However, it is likely that the pH increase (from 0.6–1.1 pH units) over the course of the ultrafiltration process, itself, caused additional protein binding of $Mg^{2+}$. Such increased binding is supported by the fact that $IMg^{2+}$ measured values were reduced by alkalinizing protein-containing solutions of $Mg^{2+}$ to higher pH values. Thus, at the lower $H^+$ concentrations, the total concentration of Mg in the ultrafiltrate is less than it would have been at pH 7.4. In addition, it is clear that not all the Mg in the ultrafiltrates is ionized. Twenty-one percent of the plasma ulhrfiltrate Mg is bound [(0.57–0.45)/0.57×100)].

The percentage of $Mg^{2+}$ bound to ligands and protein may remain remarkably constant for a given patient, albeit far from the typical ratio seen across all patients, even when TMg is changing markedly such as in coronary bypass patients; or the percentage bound may change appreciably within hours. The total Mg concentration or the ultrafilterable Mg concentration in a given sample thus cannot be used to predict the level of ionized $Mg^{2+}$ in the plasma or serum. This clearly indicates that monitoring the ionized $Mg^{2+}$ level rather than total magnesium or the ultrafilterable Mg concentration is a valuable diagnostic and prognostic parameter in critical care and acute medial care settings.

TABLE 6

Regression Analysis of Total Mg and Ionized $Mg^{2+}$ in Plasma, Serum and Their Ultrafiltrates

| | | | | | y | | x | |
|---|---|---|---|---|---|---|---|---|
| Regression of y on x | n | r | Slope | Intercept | Mean | SD | Mean | SD |
| uPTMg on PTMg | 30 | 0.77 | 0.51 | 0.13 | 0.55 | 0.05 | 0.84 | 0.07 |
| uSTMg on STMg | 48 | 0.93 | 0.66 | 0.03 | 0.66 | 0.20 | 0.93 | 0.28 |
| $PMg^{2+}$ on uPTMg | 30 | 0.69 | 0.86 | 0.11 | 0.58 | 0.05 | 0.55 | 0.05 |
| $SMg^{2+}$ on uSTMg | 48 | 0.97 | 0.99 | 0.02 | 0.67 | 0.20 | 0.66 | 0.20 |
| $uPMg^{2+}$ on uPTMg | 10 | 0.64 | 0.37 | 0.24 | 0.45 | 0.03 | 0.57 | 0.05 |
| $uSMg^{2+}$ on uSTMg | 25 | 0.94 | 0.90 | −0.04 | 0.64 | 0.21 | 0.75 | 0.21 | uPTMg = ultrafilterable plasma total Mg
uSTMg = ultrafilterable serum total Mg
$uPMg^{2+}$ = ultrafilterable plasma $Mg^{2+}$ assessed with ISE
$uSMg^{2+}$ = ultrafilterable serum $Mg^{2+}$ assessed with ISE

EXAMPLE XII

Spiking Mg Into Plasma and Wwhole Blood Samples

Results in Table 7 demonstrate the effect of adding $Mg^{2+}$ ($Cl^-$ or $SO_4^2$ salt) to samples of plasma and whole blood. As expected, for plasma samples, the calculated recovery values are less than 100% indicating that added $Mg^{2+}$ is partially bound to plasma proteins. The values reported have not been corrected for displacement of plasma water by protein and lipids. The observation that the fraction of recovered $Mg^{2+}$ increases slightly with additional amounts of added $Mg^{2+}$ indicates that partial saturation of anion binding sites is likely occurring. For experiments with whole blood, a fixed amount of $Mg^{2+}$ was added (1.0 mM). The recovery levels observed with whole blood were considerably higher than would be predicted by calculating molarity based on whole blood value. This is attributed to the fact that the added magnesium salt initially dissolves in the plasma water volume of the sample rather than being evenly distributed throughout the entire sample. The large differences seen in the spiked samples may reflect differences in hematocrit or possibly the time between $Mg^{2+}$ addition and when the sample was analyzed. In addition, differences may also exist been samples in the binding capacity by plasma proteins and solutes.

TABLE 7

Spiking of MgCl$_2$ or MgSO$_4$ into Pooled Plasma and Fresh Whole Blood

| Mg$^{2+}$ Added (mM) | Pooled Plasma (0.56 mM IMg$^{2+}$) | | | Fresh Whole Blood (0.51–0.63 mM IMg$^{2+}$) | | |
|---|---|---|---|---|---|---|
| | Ideal Expected Value (mM) | Measured Value (mM) | % Recovery | Ideal Expected Value (mM) | Measured Value (mM) | % Recovery |
| 0.5 | 1.06 | 0.97 ± 0.048* | 82.0 | — | — | — |
| 1.0 | 1.56 | 1.35 ± 0.027 | 79.0 | 1.57 ± 0.017 | 2.20 ± 0.154 | 163.0 |
| 1.5 | 2.06 | 1.78 ± 0.052 | 81.3 | — | — | — |
| 2.5 | 3.06 | 2.68 ± 0.103 | 84.8 | — | — | — |

N = 3–6 experiments each
*+Results are means ± S.E.M.

EXAMPLE XIII

Comparing IMg$^{2+}$ to TMg in CPB Patients

Figure 6:
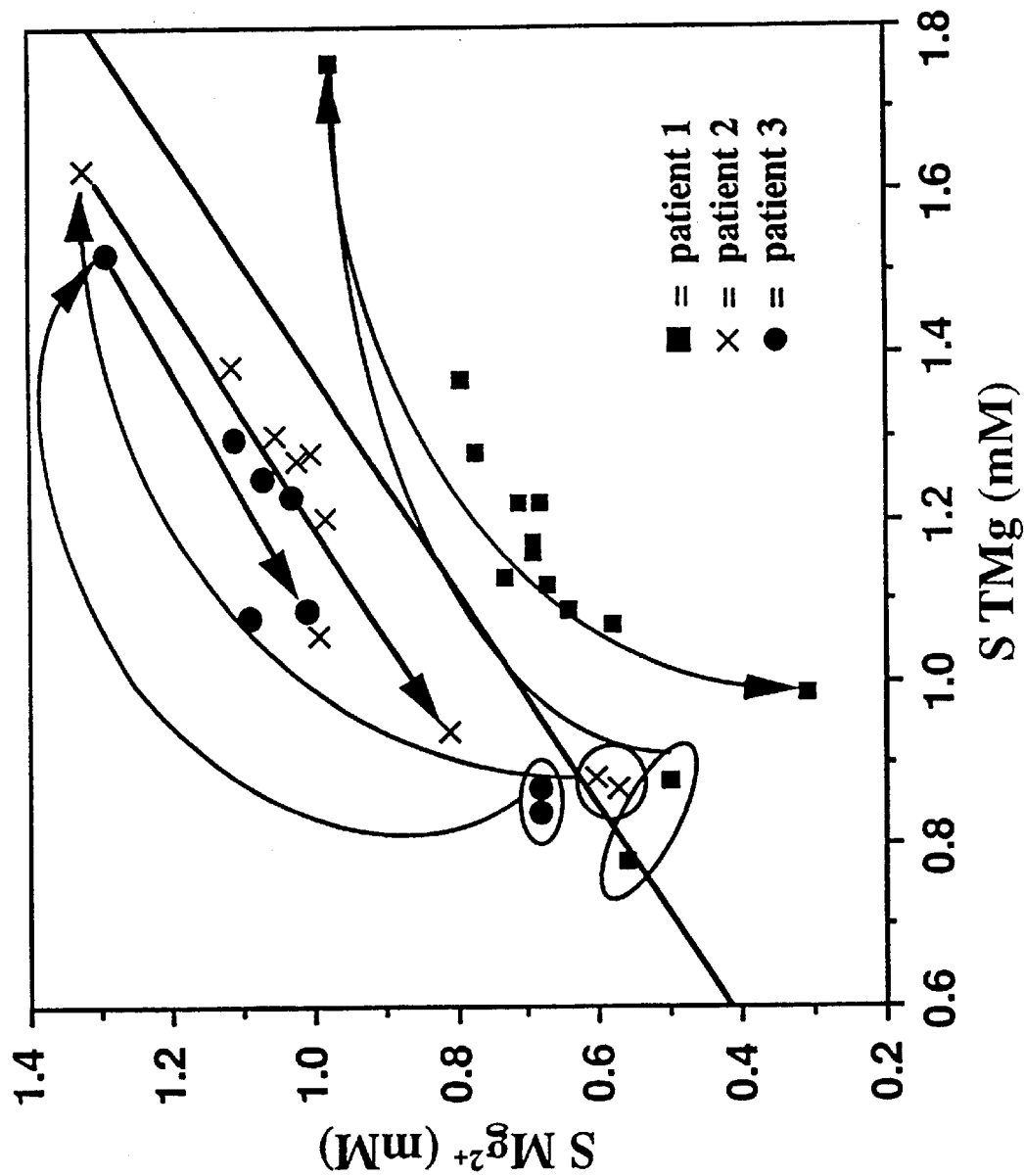
FIG. 6 $Mg^{2+}$ ($IMg^{2+}$) and TMg in three patients undergoing cardiac surgery. $Img^{2+}$ and TMg were followed in three cardiac patients perioperatively. For each patient, two samples were obtained prior to the addition of cardioplegia (circled). The first samples obtained following the addition of cardioplegia (which contained magnesium salt) demonstrated large increases in both the $Mg^{2+}$ and the TMg values (arrows left to right). As surgery progressed, both values decreased in each patient as indicated by the arrows drawn right to left. The xy line is that seen in FIG. 3: y=0.71x+0.01. The average $IMg^{2+}$/TMg ratio followed by the range of ratios for each patient were as follows: filled circles, 0.87 (0.78–1.01); Xs, 0.80 (0.66–0.93); filled squares, 0.57 (0.31–0.72).

Results shown in FIG. 6 are subset of data from FIG. 5 which showed that the level of TMg in a given sample cannot be used to predict IMg$^{2+}$. Results plotted in FIG. 6 are TMg and IMg$^{2+}$ values for several samples from each of three patients over the course of their cardiac surgeries. The first two samples from each patient, taken before cardioplegia containing Mg$^{2+}$ was administered, had values near the regression line taken from the data in FIG. 6. Following induction of cardioplegia, levels of TMg and IMg$^{2+}$ increase significantly (arrows left to right) while subsequent samples demonstrated a gradual decrease in both parameters (arrows to the left). These results show that not only did the ratio of IMg$^{2+}$/TMg differ between three patients, but it remained relatively constant within a patient during the course of the perioperative period. In other patients, the IMg$^{2+}$/TMg ratio changed significantly during this period.

EXAMPLE XIV

Cellular and Extracellular Distribution of MG

Having the information on the precise concentrations of extracellular ionized Mg in human blood allows one to determine the cellular and extracellular distribution of Mg. Using $^{31}$P-nuclear magnetic resonance spectroscopy and digital image analysis on cardiac myocytes, vascular smooth muscle cells and intact brain, the intracellular free ionized Mg$^{2+}$ was determined to be approximately 600–700 micromolar (Altura, B. M. et al. Influence of Mg$^{2+}$ on Distribution of Ionized Ca$^{2+}$ in Vascular Smooth Muscle and on Cellular Bioenergetics and Intracellular Free Mg$^{2+}$ and pH in Perfused Hearts Probed by Digital Imaging Microscopy. In: Imaging Technique in Alcohol Research, S. Zhakari, H. Witt (Eds.), NIAAA; Wash., D.C. Gov't Printing Office, 1992; Altura, B. M. et al. *J. Magn. Reson. Imaging,* 1992, in press; Barbour, et al. FASEB J. 1989, 3: A250; Barbour, et al. *Magnesium and Trace Elem.,* 1992, in press; Zhang, A. et al, *Biochem. Biophys. Acta Mol. Cell Res.* 1992, in press). Concentrations of ionized Mg$^{2+}$ across mammalian cell membranes were quite similar, that is about 500–600 micromolar. Although the relative concentration of IMg$^{2+}$ outside cells is about 71% of the total extracellular Mg, the relative amount of intracellular free ionized Mg is much less, only about 3%–6%.

EXAMPLE XV

Diagnosis & Prognosis in Cardiovascular Disease

It has been suggested that abnormalities in Mg metabolism may play an important role in the etiology of cardiac diseaes (Altura, B. M. Drugs 28 (Suppl.I):120–142, 1984; Altura, B. M. et al. In: *Metal Ions in Biological Systems* Vol 26, 1990; Iseri, C. T. West. J. Med. 138:823–828, 1983; Ebel, H. et al. J. Clin. Chem. Clin. Biochem. 21:249–265, 1983; Altura, B. M. et al. Magnesium 4:226–244, 1985; Sjogren, A. et al. J. Intern Med. 226:213–222, 1989; Zaloga, G. P. et al. In:*Problems in Critical Care* Vol 4, 1990; Rudnick, M. et al. APMIS 98:1123–1127, 1990). Although elevated extracellular Mg$^{2+}$ is widely used in connection with cardiopulmonary bypass (CPB) procedures, it is not known whether such procedures result in rapid and sequential alterations in blood ionized Mg$^{2+}$ levels. By using the methods of the present invention, ionized Mg$^{2+}$, along with ionized Ca$^{2+}$ levels in plasma were monitored in patients prior to, during, and after CPB. The patients studies ranged in age from 10–80 yrs. and were scheduled for coronary bypass, valve replacement or other elective open-heart procedures (OHP). On the basis of studies with 30 human subjects prior to and during cardiopulmonary bypass (CPB), subjects had lower than normal ionized Mg$^{2+}$ prior to surgery (Altura, B. T. et al. Clin. Chem. (July–August), 1991; Altura, B. T. et al. Clin. Res., in press; Altura, B. T. et al. Magnesium and Trace Elements, in press). Assessment of ionized Mg$^{2+}$ in plasma revealed the following [means±S.E.M. in millimolar conc. (mM)]: prior to OHP= 0.56±0.03 vs. 0.60±0.005 (control); within 10–15 minutes of CPB=0.89±0.08; post perfusion=0.75±0.03. In addition, on the basis of frequent determinations during CPB, using an ion selective electrode the degree of spontaneous hypotension, arrhythmias, and coronary vasospasm during and post-surgery were correlated to the pronounced alterations in ionized Ca$^{2+}$:ionized Mg$^{2+}$ ratios. (Altura, B. T. et al. Clin. Res., in press; Altura, B. T. et al. Magnesium and Trace Elements, in press). With respect to ionized Ca$^{2+}$, the respective values were 0.96±0.016 vs. 1.21±0.01; 0.79±0.02; and 1.23±0.10. Although the normal ionized Ca$^{2+}$:ionized Mg$^{2+}$ ratio is 1.95–2.18, all patients studied prior to CPB exhibited lower values (mean=1.72±0.09). Within 10–15 minutes of initial CPB, the ionized Ca$^{2+}$:ionized Mg$^{2+}$ ratio fell almost 50% (mean=0.91±0.10); post-perfusion, the ratio rose to 1.62±0.18. Overall, these data indicate that ionized Mg$^{2+}$ concentrations can be monitored in plasma during CPB. Predictable patterns arose out of these studies, showing that cardiac disease patients tend to exhibit lower than normal ionized Mg$^{2+}$, ionized Ca$^{2+}$ and ionized Ca$^{2+}$:ionized Mg$^{2+}$ ratios. Additionally, the hypotension observed upon initiation of CPB may in part be a reflection of elevated ionized Mg$^{2+}$ and a pronounced drop in the ionized Ca$^{2+}$:ionized Mg$^{2+}$ ratio. Such patterns are therefore diagnostic and predictive, thus allowing the physician and surgeon to carefully monitor and treat such cardiac patients.

EXAMPLE XVI

Diagnosis & Prognosis in Head Trauma

The present studies were undertaken to determine if head trauma was associated with deficits in serum, plasma and whole blood ionized $Mg^{2+}$ and to determine if the degree of head injury would correlate with the degree of the plasma ionized Mg2+ deficiency. Head trauma patients clearly demonstrated that head trauma and the degree of head trauma was associated with deficiencies in ionized $Mg^{2+}$. The range of ionized $Mg^{2+}$ in plasma of these head trauma cases was significantly below normal the greater the degree of head trauma (as assessed by clinical signs and Glasgow scores), the greater the deficit in ionized $Mg^{2+}$.

Sixty-six patients (male=44; females=22), presented in the emergency room of a large community hospital; ranging in age from 12–83 yrs., were studied. Patients with blunt head trauma were studied within 1–8 hrs of the event and compared with 60 age-matched controls and 14 patient controls with minor peripheral trauma such as cuts and sprains. A group of normal, healthy age-matched human volunteers were also employed in the study. Motor vehicle accidents (n=43) accounted for 65% of the cases, assaults (n=19) 29%, and falls (n=4) 6% of the cases. Brain injury was the sole medical problem in 59 of the patients, while associated skull fractures were present in seven cases. Criteria for exclusion included: 1. severe renal damage; 2. multiple peripheral injuries; 3. cardiopulmonary problems; 4. hypertension; and 5. diabetes. In addition, patients on low dietary magnesium intake and on certain drugs causing hypomagnesemia such as diuretics, antibiotics, digitalis, etc. were excluded. Patients with known histories of alcohol abuse (n=6) and drug abuse (i.e., cocaine, n=2) were included because they were of interest. Three patients had blood alcohol levels>200 mg/dl.

Bloods were drawn by venipuncture for routine serum laboratory chemistries (e.g. electrolytes, glucose, BUN, blood gases, creatinine) in most grade, II subjects and all grade II subjects as well as healthy control subjects and processed by automated analyzers. In addition, blood was, drawn (anaerobically) for $IMg^{2+}$, TMg and $ICa^{2+}$ by venipuncture using standard red-top Vacutainer tubes. The latter was centrifuged (3000–4000 pm) for 10–15 min after clotting and processed with a novel ion selective electrode (ISE) for $IMg^{2+}$ using a NOVA Biomedical Stat Profile 8 Analyzer which can yield measurements within 2 min. Total Mg was measured by atomic absorption spectrophotometry using a Perkin-Elmer Model Zeeman 500 and a Kodak Ektachem DT-60. The mean values using either technique were identical. In solution, sera of these patients were also processed for levels of ionized calcium ($ICa^{2+}$), sodium, potassium and hydrogen ions using selective electrodes. In order to maintain normal pH, precautions were taken to maintain the samples anaerobically. Precautions were also taken to prevent hemolysis, and most blood samples were analyzed the same day. In some cases, the latter was not possible, and in these cases the fresh anaerobically-drawn sera were frozen at −10° C. and were analyzed the next day.

Fifteen patients were administered IV fluids (<1000 ml) when blood was drawn. Similar control infusions were given to some patients in order to determine if this degree of hemodilution, per se, had any significant influence on the observed ionized hypomagnesemia.

All patients underwent complete neurological examinations and CT scans, except a few (n=3) without loss of consciousness (LOC) who did not have CT scans. The patients were divided into three groups and graded according to severity of HT: grade I (n=8) had no LOC; grade II (n=52) had concussions, sudden brief traumatic disturbance of brain function including LOC but without demonstrable anatomic lesion of brain on CT scan; and grade III (n=6) had sudden traumatic disturbance of brain function associated with identifiable CT lesion of brain tissue.

Mean values were calculated for serum $IMg^{2+}$, total Mg (TMg), $ICa^{2+}$, $ICA^{2+}/IMg^{2+}$ and percent ionized Mg ($IMg^{2+}$/TMg×100). Mean values±S.E.M. were compared for statistical significance using Students "t" test, paired t test and ANOVA with Scheffes' contrast test, where appropriate. Correlation coefficients, where appropriate, were also calculated using the method of least squares. A "P" value <0.05 was considered significant.

The studies showed that acute head trauma is associated with early deficits in $IMg^{2+}$, which are related to the severity of the injury (Table 8). However, TMg values were not significantly different between grade I, grade II or grade II HT, when compared to normal, healthy human subjects or patient controls (data not shown, identical to healthy, human subjects). Severe head trauma (grade III) resulted in significant depression of $IMg^{2+}$. The ionized fraction of magnesium in serum of head trauma patients demonstrate a progressive loss consonant with the severity of the head trauma (Table 8). Administration of IV fluids (1000 ml) did not significantly alter either the $IMg^{2+}$ or % $IMg^{2+}$ in the HT patients.

TABLE 8

Serum Ionized, Total and Percent Ionized Magnesium After Head Trauma

| PARAMETERS | CONTROLS | DEGREE OF HEAD TRAUMA | | |
|---|---|---|---|---|
| | | GRADE I | GRADE II | GRADE III |
| $IMg^{2+}$ (mM/L)* | 0.585 ± 0.005 (60)+ | 0.55 ± 0.007** (8) | 0.49 ± 0.014** (52) | 0.44 ± 0.03** (6) |
| TMg (mM/L) | 0.81 ± 0.008 (60) | 0.823 ± 0.015 (8) | 0.792 ± 0.020 (52) | 0.73 ± 0.04 (6) |
| % $IMg^{2+}$ | 71.6 ± 0.58 (60) | 66.8 ± 1.13** (8) | 63.1 ± 1.78++ (52) | 60.0 ± 1.00** (6) |

*$IMg^{2+}$ = ionized magnesium; TMg = total magnesium; % $IMg^{2+}$ = % ionized serum Mg
+Number of subjects. Patients control values were virtually identical to healthy volunteers.
**Significantly different from controls and all other values (P < 0.01).
++Significantly different from controls (P 0.01).
***Significantly different from controls and grade I HT (P < 0.01).

Comparison of the subgroups of head injury patients showed no difference between $IMg^{2+}$ levels in motor vehicle accidents (MVA's), assaults, or falls (Table 9) but all mean values were significantly depressed compared to controls. Although mean values for TMg in these three types of etiologies varied from controls there were no differences in TMg between these patients. However, there were significant differences in % $IMg^{2+}$ between the three types of initiating circumstances, i.e., falls produced the greatest deficit in % $IMg^{2+}$ with MVA's producing the least.

TABLE 9

Serum Ionized, Total and Percent Ionized Magnesium After Head Trauma Caused by Motor Vehicle Accidents, Assaults and Falls

| PARAMETERS | CONTROLS | Etiology of HT | | |
| --- | --- | --- | --- | --- |
| | | MVA | ASSAULTS | FALLS |
| $IMg^{2+}$ (mM/L) | 0.585 ± 0.005 (60)+* | 0.53 ± 0.007+ (43) | 0.53 ± 0.018+ (19) | 0.545 ± 0.011+ (4) |
| TMg (mM/L) | 0.81 ± 0.008 (60) | 0.79 ± 0.012 (43) | 0.827 ± 0.032 (19) | 0.92 ± 0.062 (4) |
| % $IMg^{2+}$ | 71.6 ± 0.58 (60) | 66.9 ± 0.91+ (43) | 64.1 ± 1.73+ (19) | 59.0 ± 2.59** (4) |

*Number of subjects
+Significantly different from controls (P < 0.01)
**Significantly different from controls and MVA (P < 0.01)

Acute head trauma was associated with early deficits in $ICa^{2+}$, which was related to the severity of the injury (Table 10). Very severe head trauma (grade III) resulted in almost a 20% depression of $ICa^{2+}$, and there was a significant increase in the relative amount of $ICa^{2+}$ to $IMg^{2+}$. However, none of the other serum analytes measured, including sodium and potassium, or hydrogen ions demonstrated any abnormalities.

TABLE 10

Serum Ionized Calcium And Ionized Calcium to Magnesium Ratios After Head Trauma

| DEGREE OF HEAD TRAUMA | $ICa^{2+}$ (mM/L) | $ICa^{2+}/Mg^{2+}$ |
| --- | --- | --- |
| Controls | 1.19 ± 0.015 (60) | 2.05 ± 0.053 (60) |
| Grade I | 1.06 ± 0.015* (8) | 1.93 ± 0.11 (8) |
| Grade II | 1.01 ± 0.02* (52) | 2.06 ± 0.08 (52) |
| Grade III | 0.96 ± 0.02+ (6) | 2.23 ± 0.034+ (6) |

$ICa^{2+}$ = ionized calcium
() = number of subjects
*Significantly different from controls (P < 0.001)
+Significantly different from controls and grade I head trauma. (P < 0.01)

Although patients with isolated skull fractures all exhibited significant deficits in serum $IMg^{2+}$ and $ICa^{2+}$ when compared to patients with grade I head trauma, these values were not lower than those seen for grade II HT and were not as low as seen in grade III HT (Table 11).

TABLE 11

Serum Ionized Magnesium, Ionized Calcium, Total and Percent Ionized Magnesium in Acute Head Trauma Patients with Isolated Skull Fractures

| $IMg^{2+}$ (mM/L) | $ICa^{2+}$ (mM/L) | TMg | % $IMg^{2+}$ |
| --- | --- | --- | --- |
| 0.51 ± 0.02* | 0.98 ± 0.043** | 0.79 ± 0.07 | 64.6 ± 1.36+ | n = 5 subjects
*Significantly different from controls and grade I HT (Table 8, P < 0.02)
**Significantly different from controls and grade I HT (Table 10, P < 0.05)
+Significantly different from controls and grade III HT (Table 8, P < 0.02)

Patients with histories of alcohol abuse or drunk on arrival in the emergency room (blood alcohol >200 mg/dl) showed significant deficits of $IMg^{2+}$ and $ICa^{2+}$ when compared with patients with cocaine abuse or control groups (Table 12). In addition, there was a significant increase in the relative amount of $ICa^{2+}$ compared to $IMg^{2+}$.

TABLE 12

Serum Ionized Magnesium, Ionized Calcium, Total and Percent Ionized Magnesium in Acute Head Trauma Patients with Alcohol Abuse

| $IMg^{2+}$ (mM/L) | $ICa^{2+}$ (mM/L) | TMg (mM/L) | % $IMg^{2+}$ | $Ca^{2+}/mg^{2+}$ |
| --- | --- | --- | --- | --- |
| 0.48 ± 0.029* | 1.05 ± 0.044 | 0.748 ± 0.059 | 64.7 ± 2.53 | 2.22 ± 0.12 | n = 6 subjects
*Significantly different from controls and grade I HT (Table 8, P < 0.01)
**Significantly different from controls (Table 10, P < 0.01)

The findings provide the first evidence for divalent cation changes in, blood early after traumatic brain injury which are of diagnostic value in the assessment of the severity of head injury, making estimations of prognosis in such patients more reliable. The method of analyzing ionized magnesium and ionized calcium can be used to monitor the response of HT to therapeutic intervention. In addition, the findings support early intervention with Mg salts after traumatic brain injury.

EXAMPLE XVII

Diagnosis & Prognosis in Hypertension

Applicants hypothesized that many hypertensive human subjects might be expected to exhibit reduction in ionized $Mg^{2+}$ (Altura, B. M. et al. Federation Proc. 40:2672–2679, 1981; Altura, B. M. et al. Science 223:1315–1317, 1984) and that treatment of such hypertensive subjects would restore ionized $Mg^{2+}$ to normal. Therapy of such patients should be signified by adjustments of plasma ionized $Mg^{2+}$ and would be a valuable adjunct for diagnosis and treatment of such patients. Data on more than 30 normotensive (0.52–0.67 mM), untreated hypertensive (0.42–0.60) and treated hypertensives (0.56–0.63), using the methodology of the present invention, supported this idea.

Ionized magnesium, serum total magnesium, and plasma renin activity (PRA) in fasting normotensive (NT) (n=20), essential hypertensive (n=28) subjects was monitored before, and 60, 90, 120 and 180 minutes after oral glucose loading (100 gm). Results were compared to intracellular free magnesium values obtained at the same time intervals as measured using $^{31}P$-NMR spectroscopy.

The average ionized $Mg^{2+}$ values in fasting normotensive subjects were 0.63±0.01 mM. Ionized $Mg^{2+}$ values in essential hypertensives, as a group, was 0.60±0.01 mM. Ionized $Mg^{2+}$ values was significantly lower for essential hypertensives who had high plasma renin activity (0.57±0.01 mM, sig=0.05 vs NT) compared to normotensives or essential hypertensives who had low plasma renin activity (0.62±0.01 mM, sig=NS vs NT).

The ionized $Mg^{2+}$ values for non-insulin dependent diabetics was consistently lower than for normotensives (0.57±0.01 mM, p<0.05 vs NT). For all subjects, fasting ionized $Mg^{2+}$ was related to Mgi (r=0.62, p<0.01).

Oral glucose loading reciprocally lowered intracellular Mg (219±12 to 193±13 $\mu$M, p<0.01), while elevating ionized $Mg^{2+}$ levels (0.60±0.02 to 0.64x0.02 mM, p<0.01). Lastly, the dynamic changes in intracellular Mg and circulating ionized $Mg^{2+}$ were also correlated (r=0.612, p<0.05). Total magnesium values did not differ in non-insulin dependent diabetics, or after glucose loading.

These data demonstrate that non-insulin dependent diabetics and essential hypertensives with high plasma renin activity have significantly lower circulating $Mg^{2+}$ than normotensives subjects.

The data also demonstrates that there is physiological transport of cellular ionic magnesium into the extrcellular space in response to oral glucose loading.

Monitoring ionized $Mg^{2+}$ concentrations in humans or animals, by the present invention, now makes it possible to diagnose, prognoses and treat hypertensive subjects.

EXAMPLE XVIII

Diagnosis and Prognosis of Patients With Idiopathic Intracranial Hypertension Idiopathic intracranial hypertension (IIH), is a well-defined syndrome of unknown etiology characterized by increased intracranial pressure (ICP), papilledema, normal intracranial anatomy and normal cerebrospinal fluid (CSP) which typically affects young obese women [Ahlskog, J. E. et al. Ann. Intern. Med. 97:249–256, 1982]. IIH has been described in association with diverse contributing factors such as certain disease states, endocrinologic abnormalities, ingestion of certain exogenous agents as well as in pregnancy and steroid withdrawal [Aslokog, J. E. et al. Ann. Intern. Med. 97:249–256, 1982; Donaldson, J. O. Neurology 31:877–880, 1981; Corbett, J. J. Can. J. Neurol. Sci. 10:22–229; 1983; Johnston, I. et al. Arch. Neurol. 48:740–747, 1991; Couban et al. Can. Med. Assn. J. 145: 657–659, 1991]. The cerebrospinal fluid in IIH is characterized as being under increased pressure, acellular in composition with normal glucose content, and normal to low-normal content. Some abnormalities have been observed in CSF in IIH, e.g., certain hormone levels appear to be elevated (i.e., vasopressin, estrone), whereas estrogen levels are often depressed [Seckl, J. et al. J. Neurol. Neurol. Neurosurg. Psychiatry 51:1538–1541, 1988; Donaldson, J. O. et al. J. Neurol. Neurosurg. Psychiatry 45:734–736, 1982; Srenson, P. S. et al. Arch. Neurol. 43:902–906, 1986]. Many investigators believe that a single underlying mechanism may be responsible for the increase in ICP. It has been suggested that IIH is a syndrome of varying brain compliance and that a vascular mechanism may have an important pathogenetic role [Johnston, I. et al. Arch. Neurol. 48:740–747, 1991; Quincke, H. Dtsch. Z. Nery. 9:140–168, 1907; Felton, W. L. et al. Neurol, 41 (Suppl.):348 (Abstr.), 1991.] It is now possible, by the present invention, to diagnose, prognoses, and treat IIH, by monitoring the levels of total Mg, $IMg^{2+}$ and ionized $Ca^{2+}$ ($ICa^{2+}$) in the serum and CSF of patients with IIH.

Patients with IIH were identified on admission to the hospital. All patients fulfilled the modified Dandy criteria for the diagnosis of IIH. All patients were obese young women. Four of five patients (subject nos. 2–5) had no history of any possible contributing factor other than obesity. One subject (subject no. 1) had a history of post-partum sagittal sinus thrombosis two years prior to entering the study. Seven cerebral spinal fluid (CSF) specimens were obtained from the five subjects after informed consent. Single specimens were obtained from subject numbers 1, 3 and 4, and two specimens each (at different times during attack) from subjects 2 and 5. Serum was obtained anaerobically after venipuncture from subjects 2, 3 and 5 during acute symptomatic exacerbations of IIH. Normal, healthy faculty and students volunteered to serve as controls.

Anaerobically-maintained serum and CSF were used to measure levels of $IMg^{2+}$, $ICa^{2+}$, sodium, potassium and H+ (pH) by ion selective electrodes. Total Mg in CSF and serum were determine by atomic absorption spectroscopy and a Kodak DT-60 Ektachem Analyzer. Percent $IMg^{2+}$ was calculated for both the CSF and serum samples. Mean values±S.E.M. were calculated and compared for statistical significance by a non-paired Student's t-test. A p-value less than 0.05 was considered significant.

The CSF levels of total Mg (TMg) were normal in all patients (Table 13). CSF levels of $IMg^{2+}$ (0.98±0.046 mM/L), $ICa^{2+}$ (0.89±0.025 mM/L) and % $IMg^{2+}$ (80.4±4.49) were considerably below the normal ranges in patients with idiopathic intracranial hypertension, CSF ionized Na+ and K+ as well as pH were normal in IIH.

TABLE 13

Ionized $Mg^{2+}$, Ionized $CA^{++}$, Total Mg and Percent Ionized Mg in Cerebral Spinal Fluid of Patients Diagnosed as Having Pseudotumor Cerebri

| Subject | mM/L | | | |
|---|---|---|---|---|
| Number | $IMg^{2+}$ | $ICa^{2+}$ | TMg | % $IMg^{2+}$ |
| 1 | 0.94 | 0.79 | 1.15 | 81.7 |
| 2 | 1.21 | 0.87 | 1.19 | 100.0 |
|  | 0.98 | 0.93 | 1.23 | 79.6 |
| 3 | 0.89 | 0.89 | 1.32 | 67.4 |
| 4 | 0.82 | 0.84 | 0.90 | 91.1 |
| 5 | 1.01 | 0.98 | 1.48 | 68.2 |
|  | 1.02 | 0.96 | 1.36 | 75.0 |
| Mean ± S.E.M. | 0.98 ± 0.046* | 0.89 ± 0.025* | 1.23 ± 0.069 | 80.4 ± 4.49* |
| Normal Range | 1.12–1.19 | 1.10–1.23 | 1.15–1.35 | 90–98 |

*Significantly different normal values (P < 0.01).

Serum levels of TMg, $IMg^{2+}$, $Ca^{2+}$, $Na^+$, $K^+$ and $H^+$ in IIH did not differ from normal, healthy subjects (Table 14). Our findings are compatible with the idea that ionic aberrations and alterations in vascular tone in the arachnoid granulations or permeability of the vascular walls may have important pathogenetic roles in pseudotumor cerebri. Intervention with Mg could have ameliorative actions in patients with IIH.

TABLE 14

Ionized $Mg^{2+}$, Ionized $Ca^{2+}$, Total Mg and Percent Ionized Mg in Serum of Patients with IIH Compared to Normal, Healthy Subjects

| Group | N | Mean Values (mM/L ± S.E.M.) | | | |
|---|---|---|---|---|---|
|  |  | $IMg^{2+}$ | $ICa^{2+}$ | TMg | % $IMg^{2+}$ |
| IIH | 3 | 0.60 ± 0.034 | 1.10 ± 0.115 | 0.89 ± 0.013 | 67.6 ± 3.98 |
| Controls | 23 | 0.58 ± 0.006 | 1.15 ± 0.024 | 0.85 ± 0.022 | 68.2 ± 0.84 |

EXAMPLE XIX

Diagnosis & Prognosis in Pregnancy-Induced Pre-Eclampsia, Hypertension, Convulsions and Fetal Growth Retardation Using the present method of sample processing and an ISE for measuring ionized $Mg^{2+}$, a study was undertaken to determine ionized and total Mg levels in umbilical venous and arterial blood in normal and abnormal pregnant patients. Correlations were made between $Mg^{2+}$ levels and maternal and neonatal pathological states. The study consisted of 64 pregnant patients of which 38 had no maternal or neonatal complications and 26 had one or more of the following abnormalities: toxemia, transient hypertension, gestational diabetes, premature labor during the current pregnancy or delivery prior to 38 weeks, growth retarded newborn, chorioamnionitis, or ABO incompatibility in the newborn. All APGAR scores were 9,10. There were no differences between the groups with regard to maternal age, race, parity, percentage of indigent patients, mode of delivery, epidural analgesis, use of Pitocin, use of oxygen in labor, ECA at delivery, mean birth weight or sex of newborn. Three patients in the abnormal group received Mg therapy for toxemia and had venous samples taken. The results are expressed as mean (mM)±SEM. In normal pregnancies, the mean umbilical venous plasma (or serum) ionized $Mg^{2+}$ level was 0.51±0.01 (N=38), which approximates the lower end of the normal range values in the venous plasma of non-pregnant women. The mean umbilical arterial ionized $Mg^{2+}$ level in normal pregnancies wasp 0.48±0.01 (N=24), demonstrating significant differences in the amount of ionized $Mg^{2+}$ which enters or leaves the fetus.

Pregnant women who had one or more of the various maternal pathological conditions listed above had a significantly lower mean venous plasma or serum ionized $Mg^{2+}$ level (0.44±0.014) than the normal group. The subgroup of pregnant women who exhibited transient hypertension had a mean venous ionized $Mg^{2+}$ level of 0.43±0.015, which is almost a 20% deficit compared to the normal group. Two patients that had chorioamnionitis had the lowest values of umbilical venous $Mg^{2+}$ in the entire study population, 0.25 mM and 0.38 mM. The percent of the total Mg which was ionized was 67.3±1.89 in the normal pregnancies and 64.5±2.31 in the abnormal ones, an insignificant difference. One of the patients with chorioamnionitis had only 49% ionized $Mg^{2+}$, however.

The study population consisted of mothers in labor, of which 51 were randomly selected, after a chart review revealed that they had no complications prior to labor and were greater than 37 weeks gestational age. Thirteen of these patients developed transient hypertension in labor and were evaluated separately. The remaining 38 patients comprised the normal study group. Venous blood samples from a separate group of 26 normal mothers admitted to the Labor and Delivery Suite in labor or for elective Cesarean section, and 42 samples from another group of non-pregnant healthy women, ages 19 through 45, were evaluated for comparison purposes.

Transient hypertension in labor was defined as repeated systolic blood pressures of ≧140 mmHg in the first stage of labor in patients without proteinuria or other signs of symptoms of preeclampsia and with no other complications in pregnancy. Blood pressures were measured in between contractions with the women in a semirecumbant position and the arm at heart level. Blood pressures of patients with this diagnosis were normal post-partum.

Newborns were considered large for gestational age (LGA) or small for gestational age (SGA) if they were greater than the 90th percentile or less than the 10th percentile in weight according to the nomograms of Batagglia et al. (J. Pediatr. 1967, 71:159–163). If any study neonate was admitted to the high risk nursery, the reason for the admission was to be documented. Patients in Labor and Delivery were not allowed to eat or drink anything and were given intravenous Ringers-lactate solution (Baxter Health Care Corp., Deerfield, Ill.) at 125 ml. per hour. Occasional patients received meperidine HCI (50 mg IV, Elkins Sinn, Inc., Cherry Hill, N.J.) and promethazine HCI (25 mg. IV, Elkins Sinn) for analgesia, as well as an oxytocin (Parke Davis, Morris Plains, N.J.) infusion (1–15 mU/min) for labor augmentation. When epidural analgesia or anesthesia was given, a test dose consisting of 3 ml. of 1.5% lidocaine HCI with epinephrine (1:200,000 dilution, Astra Pharmaceutical Prods., Westborough, Ma.) followed by a first dose containing the same medication was given. This was followed by a continuous infusion of bupivicaine HCI (0.083%, Astra Pharm.) and fentanyl (2 µg/ml, Elkins Sinn, Inc., Cherry Hill, N.J.). Patients who had epidural anesthesia for Cesarean sections were premedicated with a scopolamine patch (1.5 mg, CIBA-Geigy, Summit, N.J.) and a sodium citrate and citric acid oral solution (30 ml. Wirlen Drug Co., Baltimore, Md.) orally. They then received 13 to 20 ml. of 2% lidocaine and epinephrine (1:200,000, Astra Pharm.) or 15 to 20 ml. of chloroprocaine (3%, Astra Pharm.) to achieve an anesthetic block at the T4 level. Prior to epidural analgesia in labor, or epidural anesthesia for Cesarean procedures, all patients received an intravenous infusion of 1000 ml or 1500 ml, respectively, of Ringers-lactate solution over 15 minutes for prehydration.

Assessment of Serum Ionized Magnesium. Total Magnesium and Ionized Calcium

A 7 to 20 cm section of umbilical cord was double-clamped at delivery and samples of venous and arterial blood were aspirated separately, placed in plain red-stoppered Vacutainer tubes and allowed to clot at room temperature. Peripheral blood samples were also obtained in an age-matched group of normal, healthy non-pregnant women by venipuncture via Vacutainer tubes under anaerobic conditions. All blood samples were then centrifuged at 3000 g for 15 minutes under anaerobic conditions, and an aliquot of serum was removed under anaerobic conditions and stored at −20 ° C. Samples were analyzed within two weeks using a NOVA Biomedical Stat Profile 8 Analyzer (NOVA Biomedical Corp., Waltham, Mass.) to measure $IMg^{2+}$ and $ICa^{2+}$. In addition, TMg levels were measured with either atomic absorption spectroscopy (AAS) or a Kodak Ectachem DT-60 Analyzer (12). There was no significant differences for measurement of TMg between AAS or the Kodak Analyzer.

The $ICa^{2+}$ levels (95% confidence intervals) for both umbilical vein and artery had much wider ranges than those for $IMg^{2+}$, i.e., 0.97–1.09 mmol/l for the artery and 1.11–1.23 mmol/l for the vein. For maternal venous blood, the $ICa^{2+}$ range was (also much wider than for $IMg^{2+}$, i.e.,) 0.87–1.28 mmol/l. In non-pregnant women the peripheral serum range was 1.10–1.30 mmol/L.

Relationships Between $IMG^{2+}$ Levels, Fractions of Mg and Levels of $ICa^{2+}$ in Umbilical Vessels of Normal Subjects Mean umbilical arterial $IMg^{2+}$ remained slightly (by 0.03 mmol/l) but significantly ($p<0.05$) lower than umbilical venous $IMg^{2+}$ in the normal patients (Table 15), but there was a highly significant correlation ($r=0.79$) between both values ($p<0.0001$). The differences in the TMg between the cord blood in the two vessels were not significant, and the arterial TMg was highly correlated with the venous TMg ($r=0.76$) ($p<0.0001$). Arterial $IMg^{2+}$ also correlated with arterial total Mg ($r=0.56$) ($p<0.01$) and similarly, venous $IMg^{2+}$ correlated with venous total Mg ($r=0.69$) ($p<0.0001$).

TABLE 15

Ionized $Mg^{2+}$, Total Mg and % $IMg^{2+}$ in Umbilical Arterial and Venous Cord Blood of Normal Subjects

| Arterial | | | Venous | | |
|---|---|---|---|---|---|
| $IMg^{2+}$ (mmol/l) | TMg (mmol/l) | % $IMg^{2+}$ | $IMg^{2+}$ (mmol/l) | TMg (mmol/l) | % $IMg^{2+}$ |
| 0.48 ± 0.01 (24)* | 0.76 ± 0.02 (23) | 63.5 ± 1.87 (22) | 0.51 ± 0.001** (38) | 0.72 ± 0.01 (38) | 70.2 ± 0.94*** |

Values are means ± S.E.M.
*Represents number of different subjects.
**Significantly different from arterial $IMg^{2+}$ ($p < 0.05$)
***Significantly different from arterial % $IMg^{2+}$ ($p < 0.01$)

Mean levels±S.E.M.) of the cations and of the fractions of $IMg^{2+}$ were calculated for each patient and control group. An attempt was made to see if there were any correlations between the levels determined and clinical parameters and if there were any relationships between the cations. The numbers of samples within each subgroup varied due to sample loss. Statistical analyses were performed using the SPSS statistical package (Notusis, M. J. SPSS/PCAT Release 3.1, Chicago, SPSS Inc., 1986) for the unpaired Student's t test, Chi-square analysis, and Pearson's correlation coefficient. All results are expressed as means±standard error of the mean (SEM) unless otherwise indicated. A p value of less than 0.05 was considered significant.

Ranges of $IMg^{2+}$, Total Mg, %$IMg^{2+}$ and $ICa^{2+}$

The $IMg^{2+}$ levels for both umbilical vein and artery, and the maternal vein, of the pregnant subjects remained within narrow ranges, i.e. 0.49–0.53 mmol/l, 95% confidence interval for the umbilical vein; 0.46–0.53 mmol/l, 95% confidence interval for the umbilical artery; and 0.46–0.51, 95% confidence intervals for the maternal venous blood. In non-pregnant women the serum range was 0.55–0.67 mmol/L. The ranges for total Mg were 0.70–0.745 mmol/l for the umbilical vein, 0.70–0.78 mmol/l for the umbilical artery, and 0.74–0.82 mmol/l for maternal blood. In non-pregnant women, the serum range was 0.70–0.98 mmol/L. The ranges for the ionized fractions were 68.6–72.2% for the umbilical vein, 61.5–67.8% for the umbilical artery, and 60.5–65.1% for maternal venous blood. In non-pregnant women, the serum % $IMg^{2+}$ ranges from 67.2–75.2%.

The ionized fraction of Mg was significantly lower in the umbilical arteries than in the veins ($p<0.01$) and in both vessels the fractions were negatively correlated with the TMg levels ($r=-0.42$, $p<0.05$ in arteries and $r=0.54$, $p<0.001$ in the veins). In other terms, as the TMg rises, the % $IMg^{2+}$ falls.

The mean $ICa^{2+}$ level in the umbilical vein (1.20±0.02 mmol/L) was significantly higher than in the umbilical artery (1.03±0.03 mmol/L) ($p<0.001$). The umbilical arterial $ICa^{2+}$ level was significantly correlated to the $IMg^{2+}$ level ($r=0.44$, $p=0.02$), but this type of correlation was not seen in the vein. On the other hand, the $ICa^{2+}$ levels correlated with the Mg fractions in both the umbilical artery ($r=0.28$, $p<0.01$) and. umbilical vein ($r=0.28$, $p<0.01$) and umbilical vein ($r=0.532$, $p<0.05$).

Comparison of Relationships Between $IMg^{2+}$ Levels, Fractions of Mg and Levels of $ICa^{2+}$ in Peripheral Venous Blood Samples of Normal Pregnant and Non-pregnant Women with Samples from Umbilical Vessels The mean level of $IMg^{2+}$ in the peripheral venous blood of normal, pregnant women (0.485±0.01, n=26) was slightly but significantly less than that in the umbilical vein (Table 15) ($p<0.05$) and similar to that in the umbilical artery. The mean TMg in the peripheral blood of the mother (0.78±0.02, n=26) was significantly higher than in the umbilical vein ($p<0.001$), and the ionized fraction of Mg in the mother (62.2%) was significantly less than in the umbilical vein ($p<0.001$), and the ionized fraction of Mg in the mother (62%) was significantly less than in the umbilical vein (p<0.001), but similar to that in the artery. In the maternal veins, as in the umbilical vessels, the $IMg^{2+}$ levels correlated with the total Mg levels (r=0.44, p<0.01 for both), and the $IMg^{2+}$ ionized fraction was negatively correlated with the total Mg (r=−0.48, p<0.01).

As in the umbilical arteries, maternal venous $ICa^{2+}$ (1.09±0.01 mmol/l) positively correlated (r values=0.5–0.6, p<0.002) with both maternal venous $IMg^{2+}$ levels and with Mg fractions (p<0.01 for both). Also, as with umbilical arterial blood, this maternal peripheral venous $ICa^{2+}$ level was significantly less than the umbilical venous level (p<0.001). In contrast to these values, the peripheral venous $IMg^{2+}$ of non-pregnant, age-matched healthy women is approximately 15–20% higher (0.60±0.0005 mmol/L, n=42) than that of umbilical cord blood or maternal venous blood of women in labor. The peripheral venous TMg and % $IMg^{2+}$ in the non-pregnant age-matched healthy women are 0.83±0.06 mmol/L and 71.6±0.58%, respectively.

Correlation of Demographic Variables with $IMg^{2+}$ and $ICa^{2+}$ Levels and Fractions in Umbilical Vessels of Normal Patients In the normal study group, the maternal age ranged from 19 to 40 years, gestational age from 37.5 to 42.0 weeks, and birthweight from 2,608 to 4,706 grams. Within those ranges, there were no significant correlations between umbilical arterial or venous levels of $IMg^{2+}$, TMg or ionized fraction of $Mg^{2+}$ and the maternal or gestational ages and birthweights (Pearson's correlation coefficient p>0.05). However, there was a positive correlation between umbilical arterial $ICa^{2+}$ and birthweight (r=0.36, p=0.04).

Multiparous patients had approximately an 8% lower mean umbilical venous $IMg^{2+}$ than primiparous patients, (0.49±0.01[n=24], versus 0.53±0.02 mmol/l [n=13] p=0.02. Differences in TMg levels or fractions were not significantly different nor were there differences in the arterial samples.

There were no differences between clinic and private patients in mean $IMg^{2+}$, TMg levels, % $IMg^{2+}$ or $ICa^{2+}$ levels.

With regard to race, Blacks and Hispanics had similar levels of umbilical arterial and venous $IMg^{2+}$ compared to Whites, but Asians had approximately 8% and 27% higher mean venous and arterial $IMg^{2+}$ levels when compared to Whites (0.54±0.02 mmol/L versus 0.50±0.01 mmol/L venous, and 0.57±0.02 versus 0.45±0.01 mmol/L arterial, p=0.01 and 0.001, respectively). The percent ionized $Mg^{2+}$ fractions, however, did not differ between Asians and Whites. On the other hand the percent ionized $Mg^{2+}$ was significantly higher in Blacks than Whites in the umbilical vein (73.5±1.3 versus 68.8±1.1, p=0.03). In Hispanics, the mean TMg level in the umbilical veins was significantly lower than that of Whites (0.66±0.02 versus 0.73±0.02, p=0.04).

$ICa^{2+}$ levels also showed some variation with race. Asians appeared to have the highest mean umbilical venous $ICa^{2+}$, compared to Whites (1.27±0.04 versus 1.19±0.03 mmol/L) but this difference did not achieve statistical significance. The umbilical arterial $lCa^{2+}$ of Hispanics was almost significantly higher than that of Whites (1.12±0.04 versus 0.99±0.05 mmo/L, p=0.06).

Influence of mode of Delivery and Medications on 1 $Mg^{2+}$ Levels, Mg Fractions and $1Ca^{2+}$ Levels As seen in Table 16, there were no significant differences in arterial or venous $IMg^{2+}$, TMg and $\%IMg^{2+}$ levels in patients delivered by Cesarean section compared to those who had spontaneous vaginal delivery. But patients with operative vaginal delivery had both increased arterial and venous $IMg^{2+}$ (p<0.05) and venous TMg (p=0.04) compared to patients with spontaneous vaginal delivery. $ICa^{2+}$ levels did not vary with mode of delivery.

TABLE 16

Ionized Magnesium Levels and Fractions and Ionized $Ca^{2+}$ Levels in Umbilical Arteries and Veins of Normal Patients Versus Mode of Delivery and Anesthesia

|  |  | $IMg^{2+}$ | Total Mg | % Ionized | $ICa^{2+}$ |
|---|---|---|---|---|---|
| Mode of Delivery: |  |  |  |  |  |
| NSVD | v | 0.51 ± 0.01 (21) | 0.72 ± 0.02 (21) | 69.8 ± 1.1 (21) | 1.22 ± 0.02 (21) |
|  | a | 0.48 ± 0.01 (12) | 0.75 ± 0.03 (11) | 63.9 ± 2.3 (11) | 1.06 ± 0.04* (12) |
| Vaginal Operative | v | 0.55 ± 0.22** (5) | 0.80 ± 0.04** (5) | 68.8 ± 2.7 (5) | 1.21 ± 0.09 (5) |
|  | a | 0.57 ± 0.03** (3) | 0.82 ± 0.04 (3) | 69.7 ± 0.38 (3) | 1.10 ± 0.07 (3) |
| Cesarean | v | 0.49 ± 0.01 (11) | 0.69 ± 0.02 (11) | 72.0 ± 1.6 (11) | 1.17 ± 0.03 (11) |
|  | a | 0.45 ± 0.02 (18) | 0.71 ± 0.02 (17) | 63.9 ± 2.3 (16) | 0.98 ± 0.05 (18) |
| Use of Epidural: |  |  |  |  |  |
| yes | v | 0.50 ± 0.01 (25) | 0.70 ± 0.02 (25) | 70.9 ± 1.1 (25) | 1.20 ± 0.02 (25) |
|  | a | 0.48 ± 0.01 (18) | 0.72 ± 0.02 (17) | 65.6 ± 15 (16) | 1.06 ± 0.03* (18) |
| no | v | 0.53 ± 0.01+ (12) | 0.75 ± 0.02 (12) | 69.3 ± 1.3 (12) | 1.20 ± 0.03 (12) |
|  | a | 0.49 ± 0.03 (5) | 0.83 ± 0.05+ (4) | 62.0 ± 4.1 (4) | 0.96 ± 0.07* (5) |

(Values are means ± SEM in mmol/l; numbers of patients in parentheses; v = vein; a = artery)
*p < 0.01 compared to vein
**p < 0.05 compared to level in same vessel of patients with NSVD
+p < 0.05 compared to level in same vessel of patients who had epidural Use of epidural analgesia or anesthesia was associated with significantly lower umbilical venous $IMg^{2+}$ levels (p=0.02). The TMg was decreased in the umbilical arteries with use of epidural. $ICa^{2+}$ levels did not vary significantly.

There were no differences in umbilical venous Mg levels or fractions of $ICa^{2+}$ levels between patients who received intravenous or intramuscular medications (e.g., meperidine, promethazine, oxytocin) versus those who did not.

Relationship Between Normal Weight Grouping of Neonates and $IMg^{2+}$ Levels, Fractions of Mg and Levels of $ICa^{2+}$ Only one infant in the normal study group was borderline SGA and, thus, comparison of cation levels was not possible for such infants. However, umbilical venous samples from 12 LGA infants, and umbilical arterial samples from 11 of such subjects were compared with average for gestational age (AGA) neonates. In the venous samples, the ionized fraction was significantly greater in the LGA infants than the AGA neonates (73.0±1.4 versus 68.8±1.1%, p<0.05). Umbilical arterial $ICa^{2+}$ was also significantly higher in the LGA group (1.10±0.04 versus 0.97±0.04 mmol/L, p<0.05).

Comparison of Demographic Variables and Outcomes Among the Different Study Groups When the different study groups were compared with regard to maternal or gestational age, percent primigravida, race, or use of analgesia or medications, no differences were found (Table 17). The increased percentages of indigent patients in the group with transient hypertension approached significance (p=0.06). Unlike the other groups, none of the patients in the transient hypersensitive group were delivered by Cesarian section (Chi-square, p=0.02).

TABLE 17

Comparison of Demographic Data, Medication in Labor, and Neonatal Outcome in the Different Study Groups

| | Diagnosis | |
|---|---|---|
| | Normal | Transient Hypertension |
| # of Patients | 38 | 13 |
| Maternal Age, yr | 27.9 ± 0.9 | 25.4 ± 1.4 |
| Race: | | |
| White | 19 (50.0) | 6 (46.0) |
| Black | 4 (10.5) | 3 (23.1) |
| Hispanic | 7 (18.4) | 3 (23.1) |
| Asian | 8 (21.0) | 1 (7.7) |

TABLE 17-continued

Comparison of Demographic Data, Medication in Labor, and Neonatal Outcome in the Different Study Groups

| | Diagnosis | |
|---|---|---|
| | Normal | Transient Hypertension |
| Primagravida | 14 (36.8) | 7 (53.8) |
| Indigent | 7 (18.4) | 6 (46.2)* |
| Mode of Delivery: | | |
| NSVD | 22 (57.9) | 10 (76.9) |
| Vaginal Operative | 5 (13.2) | 3 (23.1) |
| Cesarean Section | 11 (28.9) | 0 (0)* |
| EGA | 39.6 ± 0.21 | 39.9 ± 0.29 |
| Epidural | 26 (68.4) | 11 (84.6) |
| Meperidine HCl, promethazine HCl | 2 (5.1) | 0 (0) |
| Oxytocin | 13 (34.2) | 2 (15.4) |
| Birth Weight (g) | 3462.2 ± 79.1 | 3366.4 ± 122.4 |
| LGA | 13 (34.2) | 3 (23.1) |
| Meconium | 3 (7.9) | 1 (7.7) |
| Male Newborn | 16 (42.1) | 4 (30.8) |

(Parametric Data are Means ± SEM; numbers in parenthesis are %)
*p < 0.05 compared to normal patients
+p = 0.06 compared to normal patients There were no significant differences between the neonatal groups with regard to birthweight, macrosomia, meconium and Sec distribufion. None of the neonates of the mothers with transient hypertension were SGA. None of the neonates had significant morbidity or entered the neonatal intensive care unit.

Comparison of $IMg^{2+}$ Levels, Fractions of Mg and $ICa^{2+}$ Levels Between Normal Subjects and Transient Hypertensives The mean $IMg^{2+}$ level in the umbilical veins, but not in umbilical arteries, of transient hypertensives was significantly lower than that in normal patients (Table 18). The TMg levels were similar in the umbilical veins and arteries of both types of patients. When the mean TMg levels, $IMg^{2+}$ and mean % ionized fractions in the transient hypertensives in the artery were compared to the vein, only the % $IMg^{2+}$ was significantly different (P<0.01) from the normal subjects. Umbilical arterial $ICa^{2+}$ (1.00±0.07 mmol/l) was significantly lower (P<0.05) than umbilical venous $ICa^{2+}$ (1.17±0.003 mmol/l), as in the normal patients. However, both mean arterial and venous levels of $ICa^{2+}$ did not differ significantly from the mean levels of normal patients.

TABLE 18

Ionized $Mg^{2+}$, Total Mg and % $IMg^{2+}$ in Umbilical Arterial and Venous Cord Blood of Pregnant Women with Transient Hypertension in Labor

| Arterial | | | Venous | | |
|---|---|---|---|---|---|
| $IMg^{2+}$ (mmol/l) | TMg (mmol/l) | % $IMg^{2+}$ | $IMg^{2+}$ (mmol/l) | TMg (mmol/l) | % $IMg^{2+}$ |
| 0.44 ± 0.02 (7)* | 0.85 ± 0.13 (7) | 62.0 ± 1.68 (7) | 0.46 ± 0.01** (13) | 0.75 ± 0.07 (13) | 68.9 ± 1.53*** (13) |

Values are means ± S.E.M.
*Represents number of different subjects
**Significantly different from umbilical venous blood of normal women (P < 0.01), (Table 15)
***Significantly different from arterial % $IMg^{2+}$ (p < 0.01)

When the arteriovenous differences in the umbilical vessels for mean Mg levels and fractions were compared, we could not find any significant differences between normal pregnant women in labor and those presenting with transient hypertension in labor (Table 19).

It is known that labor induces significant elevations of serum epinephrine and norepinephrine. Deficits in [$Mg^{2+}$] are known to potentiate the contractile effects of catecholamines on all types of blood vessels, including umbilical arteries and veins. It has been shown that Mg therapy can blunt the hypertensive action of epinephrine, norepinephrine and other pressors without altering its cardiotonic action. However, patients who enter labor with a deficiency in ionized $Mg^{2+}$ may not be able to blunt the hypertensive effects of rises in norepinephrine, epinephrine or other pressor agents related to stress. The end result is that the lower than normal $IMg^{2+}$ allows more $ICa^{2+}$ to enter, and be released from, the smooth muscle cells lining the peripheral blood vessels, resulting in decreased vascular lumen sizes and increases in peripheral vascular resistance.

TABLE 19

Arteriovenous Differences in Mg Levels and Fractions in Normal Pregnant Women in Labor Compared to Those with Transient Hypertension in Labor

| Group | Arteriovenous Differences | | |
|---|---|---|---|
| | $IMg^{2+}$ (mmol/l) | TMg (mmol/l) | % $IMg^{2+}$ |
| Normal | −0.03 ± 0.01 (23)* | 0.07 ± 0.02 (22) | −9.05 ± 1.95 (22) |
| Transient Hypertension | −0.02 ± 0.01 (7) | 0.04 ± 0.02 (7) | −6.14 ± 1.42 (7) |

Values are means ± S.E.M.
*Represents number of different subjects

The overall data indicate that serum or plasma ionized $Mg^{2+}$ levels in pregnancy are of diagnostic value. Transient hypertension in labor is associated with hypomagnesemia, which could account in large measure for the increase in blood pressure. Therefore, the present methodology for use in monitoring ionized $Mg^{2+}$ concentrations throughout pregnancy allows the obstetrician to prevent pregnancy-induced pre-eclampsia, hypertension, convulsions and fetal growth retardation by treatment of the women with $Mg^{2+}$ salts which elevate ionized $Mg^{2+}$ when levels drop abnormally low. Furthermore, ionized $Mg^{2+}$ levels may be a biochemical marker for following disease processes in pregnant women and their response to treatment.

EXAMPLE XX

Ionized Magnesium and Calcium Levels in Cyclosporine Treated Renal Transplant Recipients Ionized $Mg^{2+}$ and ionized $Ca^{2+}$ were measured in 54 cyclosporine (CSA) treated renal transplant recipients (6 mos. to 7 yrs. post-transplant, mean CSA=192±19.3 ng/dl) and 34 age-matched control subjects using an ion selective electrode.

Renal transplant recipients demonstrated pronounced deficits in mean ionized $Mg^{2+}$ (0.48±0.01 vs. control 0.61±0.06 mM/L, p<0.001). These recipients demonstrated slight deficits in mean total magnesium (0.77±0.015 vs. 0.84±0.017 mM/L, p<0.001) and no change in mean ionized $Ca^{2+}$ (1.20±0.02 vs. 1.18±0.01 mM/L, p=NS).

Renal transplant recipients with plasma cholesterol <215 mg/dl and control subjects did not show a correlation between cholesterol level, ionized $Mg^{2+}$, ionized $Ca^{2+}$ or total magnesium. Both ionized $Mg^{2+}$ and total magnesium correlated positively (p<0.05) with plasma cholesterol in renal transplant recipients with plasma cholesterol levels >240 mg/dl. Renal transplant recipients with high plasma cholesterol levels also demonstrated a strong negative correlation between cyclosporine level and ionized $Mg^{2+}$ (p<0.01), i.e., patients with high cyclosporine levels having the lowest ionized magnesium values.

Renal transplant recipients with high plasma cholesterol had strong positive correlation between cyclosporine levels and ionized $Ca^{2+}$/ionized $Mg^{2+}$ ratios and a negative correlation between plasma cholesterol and ionized $Ca^{2+}$/ionized $Mg^{2+}$ ratios.

Therefore, using the method of the present invention, it has been possible to correlate cyclosporine toxicity with ionized $Mg^{2+}$ deficiencies in renal transplant recipients with hypercholesterolemia. The accelerated atherosclerosis noted in cyclosporine-treated renal transplant recipients is related to alterations in ionized $Mg^{2+}$ ratios. Ionized $Mg^{2+}$, and not total Mg, appears to be the most sensitive clinical parameter in cyclosporine-treated renal transplant recipients. Therefore, the method of the present invention in conjunction with measurements of plasma cholesterol is diagnostic and prognostic in predicting development or exacerbation of atherosclerosis in renal transplant recipients treated with cyclosporine. Therapeutic intervention with magnesium to bring the plasma levels of ionized magnesium to within the normal range of approximately 0.53–0.67 mM serves to lessen atherosclerosis in renal transplant recipients with high plasma cholesterol levels.

EXAMPLE XXI

Ionized $CA^{2+}$:$MG^{2+}$ Ratios

Since determinations of ionized $Ca^{2+}$ have been suggested to be of value in critical care medicine (Zaloga, G. P. et al. Crit. Care Med. 15:813–816, 1987; Olinger,. M. L. The Emerg. Med. Clin. N. Amer. 7:795–822, 1989) and significant alterations in ionized $Mg^{2+}$ can be measured using the present methods, it is reasonable to examine and utilize $Ca^{2+}$:$Mg^{2+}$ ratios in the diagnosis and treatment of disease states where both of these cations could be expected to exhibit subtle changes in body fluids. The data described herein, particularly for cardiac patients and such patients on cardiopulmonary bypass indicate that the $Ca^{2+}$:$Mg^{2+}$ ratios are significantly diagnostic and prognostic markers for hypotension, coronary vasospasm and dysrhythmias during and post cardiac surgery. Additionally, $Ca^{2+}$:$Mg^{2+}$ ratios may be diagnostic and prognostic in determining the severity and progression of head trauma, abnormal pregnancies, and hypotension.

Currently, it is recommended by the U.S. National Academy of Sciences that human subjects consume in their diets 900–1000 mg/day of elemented calcium (which=22.5–25 mmoles of Ca) and 350–400 mg/day of elemental magnesium (which=14.4–16.5 mmoles of Mg). This represents molar ratios (Ca/Mg) of 1.36–1.74. All current diet supplements and dietary components are based on these values. However, these values used by the U.S.A. National Academy of Sciences are based on metabolic balance studies of calcium and magnesium in human subjects. Such metabolic balance studies are based on total calcium and total magnesium balances, not on the biologically (or physiologically) active minerals, which are the ionic forms, i.e. $ICa^{2+}$ and $IMg^{2+}$.

The measurements on whole blood, plasma and serum levels of $ICa^{2+}$ and $IMg^{2+}$ by the method of the present invention, using an ion selective electrode, yield mean $ICa^{2+}$ levels of about 1.20 mM/L and $IMg^{2+}$ levels of about 0.60 mM/L. This is a molar ratio of approximately 2.00/1. Therefore, the old formulation based on total calcium and total magnesium is incorrect. Normal diets should contain a molar ratio of approximately 2.0/1.0 for Ca/Mg in order to maintain the proper blood levels of ionized $Ca^{2+}$ and ionized $Mg^{2+}$. Dietary supplements, vitamin and mineral supplements should thus be based on such a new ratio.

EXAMPLE XXII

Treatment of Headache

Methods and Materials

Forty consecutive patients who presented to the headache clinic with a moderate or severe headache of any type (4 or higher on a verbal 1 to 10 scale) were enrolled in this study after an informed consent. Some patients came in to the clinic with the purpose of participating in the study, while others had routine appointments and happened to have had a headache at the time of visit. Patients with renal, cardiac, diabetic or other medical problems were excluded. The international Headache Society classification was used to diagnose all patients.[23] Age-matched healthy volunteers served as control subjects.

Immediately prior to the magnesium infusion a blood sample of serum $IMg^{2+}$, total magnesium (TMg) and ionized calcium ($ICa^{2+}$) was drawn under anaerobic conditions. The laboratory personnel (B.T.A., B.M.A.) were blinded as the blood samples were not accompanied by any clinical information, while the clinician administering the infusion (A.M.) received test results several days after the completion of the evaluation. Serum levels of $IMg^{2+}$ and $ICa^{2+}$ were measured using ion-selective electrodes with a NOVA Biomedical Stat Profile 8 Analyzer.[16–18] The lower limit of normal for $IMg^{2+}$ levels in this study was 0.55/mmol/L. The normal range for the $ICa^{2+}/IMg^{2+}$ ratio is 1.92–2.08. In 95% of the normal controls, $IMg^{2+}$ was equal to or above 0.55 mmol/L and below 0.66 mmol/L, and $ICa^{2+}$ was between 1.15 and 1.25 mmol/L. Total Mg in the serum was determined by atomic absorption spectroscopy and a Kodak DT-60 Ektachem Analyzer, which yield identical results.[16–18] Normal serum total Mg varies between 0.70–1.05 mmol/L. Percent $IMg^{2+}$ ($\%IMg^{2+}$) and $ICa^{2+}/Mg^{2+}$ ratios were calculated.

One gram of $MgSO_4$ [Astra Pharmaceuticals, Boston Mass.] in a 10% solution was given intravenously over 5 minutes. Headache intensity was measured on a verbal 1 to 10 scale prior to and 15 minutes after the infusion. A greater than 50% reduction of pain intensity was considered a positive response. The recurrence or worsening of a headache within the following 24 was determined in a telephone interview on the following day. The clinical response to the $IMg^{2+}$ levels was correlated. The correlation was considered to be positive if patients with a normal $IMg^{2+}$ level ($\geq 0.55$ mmol/L) had no relief or less than 24 hrs of relief. In patients with low $IMg^{2+}$ levels (<0.55 mmol/L), a correlation was considered positive only if relief lasted for more than 24 hrs.

Mean values±S.E.M. were calculated and compared for statistical significance by a Student's t-test, ANOVA with Scheffe's contrast test, analysis of co-variance for age, and linear regression analysis, where appropriate. Chi-Square tests were also utilized where appropriate. A p value of less than 0.05 was considered significant.

Results

Classification and Response to IV $MgSO_4$

The first 40 patients treated included 16 patients with migraines without aura, 9 patients with cluster headaches and 15 with chronic daily headaches. The category of chronic daily headaches is not included in the original IHS classification, but several proposal for this new category have been published because some patients were not classifiable. Silberstein et al. have proposed a subdivision for characterization of headaches which includes new daily persistent headaches (NDPH) and transformed migraine (TM). Using this new subdivision, nine patients were identified with TM and two with NDPH. Patients with daily headaches were divided into those with migrainous types of headaches (i.e., three or more of the following six migraine features: presence of nausea, unilateral pain, pulsatile quality of pain, worsening of pain by light physical activity, photophobia and phonophobia) and those with daily tension-type headaches. Eleven patients with daily headaches had chronic migrainous and four had tension headaches. Of the nine patients with cluster headaches, eight had episodic cluster headaches and one had a chronic one. One patient (#1, Table 1) with a typical migraine headache was diagnosed to have acute glaucoma the day after infusion.

Almost all patients reported having a flushed feeling during the IV infusion of $MgSO_4$. No other side effects were noted. Patients who responded to the treatment were highly satisfied with the results.

TABLE 1

Serum Ionized Magnesium Levels in Patients with Different Types of Headaches Before Intravenous $MgSO^4$: Responders Versus Non-Respondees

| Patient No | Sex | Age | $IMg^{2+}$ (mmol/L) | Response | Return Within 24 hr | Correlation Resp: $IMg^{2+**}$ |
|---|---|---|---|---|---|---|
| Migraine |
| 1 | F | 45 | 0.59 | Y* | Y | Y |
| 2 | F | 47 | 0.54 | Y | Y | Y |
| 3 | F | 37 | 0.48 | Y | N+ | Y |
| 4 | F | 49 | 0.59 | Y | N | N |
| 5 | F | 48 | 0.57 | Y | Y | Y |
| 6 | F | 48 | 0.54 | N | — | Y |
| 7 | F | 52 | 0.45 | Y | Y | N |
| 8 | F | 41 | 0.54 | Y | Y | Y |
| 9 | F | 42 | 0.42 | Y | N | Y |
| 10 | F | 33 | 0.50 | Y | N | Y |
| 11 | F | 36 | 0.48 | Y | N | Y |
| 12 | M | 31 | 0.60 | Y | N | N |
| 13 | F | 29 | 0.52 | Y | N | Y |
| 14 | F | 38 | 0.55 | Y | Y | Y |
| 15 | F | 35 | 0.58 | Y | Y | Y |
| 16 | F | 42 | 0.56 | Y | Y | Y |
| Cluster |
| 17 | M | 40 | 0.44 | Y | N | Y |
| 18 | F | 32 | 0.45 | Y | N | Y |
| 19 | M | 35 | 0.49 | Y | N | Y |
| 20 | M | 46 | 0.49 | Y | N | Y |
| 21 | M | 39 | 0.54 | Y | Y | Y |
| 22 | F | 47 | 0.60 | Y | Y | Y |
| 23 | M | 29 | 0.53 | Y | Y | N |
| 24 | M | 40 | 0.55 | Y | N | N |
| 25 | F | 31 | 0.53 | Y | N | Y |
| Chronic Migrainous |
| 26 | F | 39 | 0.52 | Y | N | Y |
| 27 | F | 14 | 0.52 | Y | N | Y |
| 28 | M | 42 | 0.45 | Y | N | Y |
| 29 | F | 45 | 0.43 | Y | Y | N |
| 30 | M | 33 | 0.51 | N | — | N |
| 31 | F | 22 | 0.55 | N | — | Y |
| 32 | F | 46 | 0.59 | N | — | Y |

TABLE 1-continued

Serum Ionized Magnesium Levels in Patients with Different Types of Headaches Before Intravenous MgSO$^4$: Responders Versus Non-Respondees

| Patient No | Sex | Age | IMg$^{2+}$ (mmol/L) | Response | Return Within 24 hr | Correlation Resp: IMg$^{2+}$** |
|---|---|---|---|---|---|---|
| 33 | F | 51 | 0.49 | N | — | N |
| 34 | F | 41 | 0.64 | Y | Y | Y |
| 35 | F | 40 | 0.59 | N | — | Y |
| 36 | F | 30 | 0.55 | Y | N | N |
| Chronic Tension | | | | | | |
| 37 | F | 51 | 0.61 | N | — | Y |
| 38 | M | 55 | 0.57 | N | — | Y |
| 39 | M | 41 | 0.50 | Y | N | Y |
| 40 | F | 34 | 0.59 | Y | N | N |

*Y = Yes
+N = No
**Correlation of response to the IMg$^{2+}$ levels was considered to be positive if either: a) patients with low IMg$^{2+}$ levels (<0.55 mmol/L) had no return of their headache within 24 hrs or b) patients with normal IMg$^{2+}$ had no response or had a response lasting less than 24 hrs.

Of the 40 patients to whom IV MgSO$_4$ was administered, 32 (80%) had at least a 50% initial reduction of pain intensity. In most patients, headaches began to improve before the end of infusion. Complete elimination of pain was observed in 80% of the patients within 5 min of infusion. Of these 32 patients, 18 had persistent relief of their headache beyond 24 hours. Of these 18 with sustained relif, 14 had a serum IMg$^{2+}$ equal to or below 0.54. Of the 22 who either did not respond or had their headache return within 24 hours, 13 had an IMg$^{2+}$ level of 0.55 mmol/L or above. In most patients whose headache returned within 24 hours, relief lasted for only 1–2 hours. Overall, in 75% of the patients there was a correlation between the clinical response to IV MgSO$_4$ and the serum IMg$^{2+}$ level (P<0.01).

Long-term responses to MgSO$_4$ varied in the different diagnostic categories. All nine patients with cluster headaches had their acute headache aborted by Mg therapy. The one patient (#17) with a chronic headache had relief for 28 hours after the initial and each of the three subsequent infusions. Repeat IMg$^{2+}$ measurements after 48 hr intervals revealed persistent low levels in most of these cluster headache patients. In two patients (#18 and #19) with episodic clusters, a single infusion of MgSO$_4$ aborted the entire cluster episode. In another two subjects (#24 and #25), with episodic clusters, headaches returned within 24 hrs, while the other four patients had relief for two-seven days. Repeat infusions of 1 to 3 gram of MgSO$_4$ each produced relief lasting approximately 48 hours. A return of headaches was accompanied by a drop in IMg$^{2+}$ levels to 0.48 mmol/L or less.

Long-term results in patients with intermittent migraine attacks is difficult to gauge because of the variable frequency of migraines in these patients. Responses in patients with chronic headaches also varied. For example, in patient #28 (Table 1) the relief lasted 24 hours, but the return of the headache was accompanied by a drop in IMg$^{2+}$ level to 0.44 mmol/L. In our youngest patient (#27), a single infusion of MgSO$_4$ produced a positive response to Mg that persists five months later, at the time of this writing. Various therapists (i.e., acetaminophen—1000 mg or ibuprofen—400 mg-four times/day; nabumetone—1000 mg/day for two weeks; cyproheptadine—4 mg nightly for two weeks; physical exercise) were tried in this patient for two months prior to the infusion with no relief.

Serum Ionized Mg, Total Mg, Ionized Calcium, Percent Ionized Mg and ICa$^{2+}$/IMg$^{2+}$ Ratio in Responders, Non-Responders and Subcategories of Headache Although the total serum Mg levels for all subcategories of headache, including responders to IV MgSO$_4$, were within the normal healthy control volunteer levels (Tables 1–3), both the non-responders and the patients presenting with chronic tension headaches exhibited an elevation of TMg compared to the responders and other subgroups (Tables 2 and 3). Patients demonstrating no return of headache or associated symptoms within 24 hrs. of IV MgSO$_4$ exhibited the lowest initial basal levels of IMg$^{2+}$ (Tables 1 and 2). Although all subcategories of headache types (except chronic tension) investigated exhibited low serum IMg$^{2+}$ during headache pain, and prior to IV MgSO$_4$, the patients with cluster headaches exhibited the lowest basal levels of IMg$^{2+}$. All headaches subjects, except for the non-responders and the chronic tension group, exhibited rather high ICa$^{2+}$/IMg$^{2+}$ ratios; ICa$^{2+}$ levels, however, were not significantly different from healthy volunteers (Tables 2 and 3). When compared to healthy age-matched volunteers, all types of headache subject, including the non-responders, demonstrated a deficit in percent IMg$^{2+}$, representing approximately an 11–18% fall-off from normal (Tables 2 and 3).

TABLE 2

Serum Ionized Magnesium, Total Magnesium, Percent Ionized Magnesium and Ionized Calcium in Healthy Volunteers versus Headache Responders and Non-Responders Before IV MgSO$_4$

| Group | N | IMg$^{2+}$ (mmol/L) | TMg (mmol/L) | ICa$^{2+}$ (mmol/L) | % IMg$^{2+}$ | ICa$^{2+}$/IMg$^{2+}$ |
|---|---|---|---|---|---|---|
| Controls | 60 | 0.60 ± 0.008 | 0.82 ± 0.009 | 1.22 ± 0.008 | 73.1 ± 0.62 | 2.03 ± 0.03 |
| All Headache Subjects | 40 | 0.531 ± 0.008* | 0.868 ± 0.012 | 1.22 ± 0.005 | 61.1 ± 0.77* | 2.33 ± 0.04* |
| Initial Responders | 32 | 0.524 ± 0.009* | 0.860 ± 0.014 | 1.22 ± 0.005 | 61.0 ± 0.91* | 2.35 ± 0.05* |
| No Return of Headache Within 24 hr | 18 | 0.503 ± 0.011+ | 0.841 ± 0.019 | 1.22 ± 0.008 | 60.1 ± 1.15* | 2.44 ± 0.06* |
| Non-Responders | 8 | 0.556 ± 0.014 | 0.901 ± 0.021** | 1.22 ± 0.014 | 61.8 ± 1.36* | 2.18 ± 0.053 |

Values are means ± S.E.M.
*Significantly different from healthy controls (P < 0.01).
+Significantly different from controls and non-responders (P < 0.05).
**Significantly different from controls (P < 0.01).

TABLE 3

Serum Ionized Magnesium, Total Magnesium, Ionized Calcium, Percent Ionized Magnesium and Ionized Calcium/Magnesium Ratio in Various Types of Headache Patients Versus Healthy Volunteers

| Headache Type | N | IMg$^{2+}$ (mmol/L) | TMg (mmol/L) | ICa$^{2+}$ (mmol/L) | % IMg$^{2+}$ | ICa$^{2+}$/IMg$^{2+}$ |
|---|---|---|---|---|---|---|
| A. Controls | 60 | 0.60 ± 0.008 | 0.82 ± 0.009 | 1.22 ± 0.008 | 73.1 ± 0.62 | 2.03 ± 0.03 |
| B. Migraine | 16 | 0.531 ± 0.013* | 0.869 ± 0.023 | 1.22 ± 0.035 | 61.4 ± 1.37* | 2.32 ± 0.26* |
| C. Cluster | 9 | 0.513 ± 0.016* | 0.847 ± 0.015 | 1.22 ± 0.011 | 60.5 ± 1.73* | 2.40 ± 0.08* |
| D. Chronic Migrainous | 11 | 0.531 ± 0.018* | 0.864 ± 0.019 | 1.22 ± 0.006 | 61.3 ± 1.44* | 2.30 ± 0.08* |
| E. Chronic Tension | 4 | 0.568 ± 0.024 | 0.925 ± 0.044* | 1.23 ± 0.03 | 61.4 ± 0.88* | 2.18 ± 0.08 |

Values are means ± S.E.M.
*Significantly different from healthy control subjects (P < 0.01).

EXAMPLE XXIII

Treatment of Headache by Oral Administration of Aqueous Magnesium $MgSO_4$ was dissolved in bottled water containing low sodium, no calcium and little or no other anions or minerals (Bartlett Springs, Calif.) in a concentration of 200–450 mg per liter of water.

Three patients having symptoms of migraine headaches imbibed 1–2 liters of the aqueous magnesium solution per day on a daily basis for over a two-year period. This provided approximately 8 to about 37 mmoles Mg per day. The headache symptoms were alleviated within two-three months of treatment. The patients remained free of headache symptoms for over two years.

EXAMPLE XXIV

Treatment of Hypo- and Hyper-Magnesemia States

Use of the present invention allows the physician, veterinarian and researcher to scientifically monitor and treat hypo or hypermagnesemia states.

Candidates for treatment with $Mg^{2+}$ or calcium and $Mg^{2+}$ include animals, particularly mammals such as humans with migraine, coronary heart disease, congestive heart failure, hypomagnesemia, critical illnesses, lung diseases, abnormal pregnancy, undergoing cardiopulmonary bypass, head trauma, aminoglycoside (or other antibiotics) toxicity, chemotherapeutic drug-induced hypomagnesemia or those in high risk categories for heart attack or stroke such as those with hypertension, diabetes, high cholesterol, or smokers and the like. Candidates for $Mg^{2+}$ treatment or $Mg^{2+}$ and $Ca^{2+}$ treatment also includes those with idiopathic intracranial hypertension, renal transplant recipients and non-insulin dependent diabetics. The amount of $Mg^{2+}$ administered will, of course depend upon the severity of the condition being treated, the route of administration chosen, and the dose of $Mg^{2+}$, and ultimately will be decided by the attending physician or veterinarian. As a guide, a concentration of $Mg^{2+}$, as used in the prior art include regimens similar to those reported by clinicians for different disease states (Wacker, W. E. C. *Magnesium and Man,* 1980; Iseri, C. T. et al. West J. Med. 138:823–828, 1983; Zaloga, G. P. In: *Problems in Critical Care* Vol 4, 1990; Rudnick, M. et al. APMIS 98:1123–1127, 1990; Rasmussen, H. S. et al. Lancet 1:234–236, 1986; Berkelhammer, C. et al. Canadian Med. Assoc. J. 312:360–368, 1985; Cohen, L. et al. Magnesium 3:159–163, 1984; Dyckner, T. et al. Brit. Med. J. 286:1847–1849, 1983; Olinger, M. L. The Emerg. Med. Clin. N. Amer. 7:795–822, 1989; Kobrin, S. M. et al. Sem. in Nephrol. 10:525–535, 1990). Use of the present methodology and assessment of ionized $Mg^{2+}$, rapidly, will make it possible to monitor a patient's response to therapeutic regimens in a precise and carefully controlled manner, which was heretofore not possible.

$Mg^{2+}$ or $Mg^{2+}$ and $Ca^{2+}$ may be administered by any route appropriate to the condition being treated including intravenous (IV), intraperitoneal, intramuscular, subcutaneous, oral, nasal, and the like. Preferably, the $Mg^{2+}$ is injected IV into the blood stream of the mammal being treated especially in acute cases of hypomagnesemia. It will be readily appreciated by those skilled in the art that the preferred route will vary with the condition being treated.

While it is possible for the $Mg^{2+}$ to be administered as the pure or substantially pure mineral, it is preferable to present it as a pharmaceutical formulation or preparation. Suitable bioavailable magnesium salts and magnesium compounds are well known in the art as described in U.S. Pat. No. 4,954,349 and U.S. Pat. No. 4,546,195, incorporated herein by reference.

The formulations for the present invention, both veterinary and for human use, comprise $Ca^{2+}$, $Mg^{2+}$ or $Ca^{2+}$ and $Mg^{2+}$ together with one or more pharmaceutically acceptable carriers and. optionally other therapeutic ingredients. The carrier(s) must be "acceptable" in the sense of being compatible with the other ingredients of the formulation and not deleterious to the recipient thereof. The formulations may conveniently be presented in unit dosage form and may be prepared by any method well known in the pharmaceutical art.

All methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then, if necessary, shaping the product into the desired formulation.

Formulations suitable for intravenous, subcutaneous, or intraperitoneal administration conveniently comprise sterile aqueous solutions of the active ingredient with solutions which are preferably isotonic with the blood of the recipient. Such formulations may be conveniently prepared by dissolving solid active ingredient in water containing physiologically compatible substances such as sodium chloride (e.g. 0.1–2.6 M), Ringers solution, parenteral solution for I.V. or oral administration and the like, and having a buffered pH compatible with physiological conditions to produce an aqueous solution, and rendering said solution sterile. These may be presented in unit or multi-dose containers, for example, sealed ampoules or vials.

The formulations of the present invention may incorporate a stabilizer. Illustrative stabilizers are polyethylene glycol, proteins, saccharides, amino acids, inorganic acids, and organic acids which may be used either on their own or as admixtures. These stabilizers are preferably incorporated in an amount of 0.11–10,000 parts by weight per part by weight of mineral. If two or more stabilizers are to be used their total amount is preferably within the range specified above. These stabilizers are used in aqueous solutions at the appropriate concentration and pH. The specific osmotic pressure of such aqueous solutions is generally in the range of 0.25–0.35 osmoles, preferably in the range of 0.29–0.32. The pH of the aqueous solution is adjusted to be within the range of 7.0–8.0, preferably within the range of 7.2–7.6. In formulating the therapeutic agent of the present invention, anti-adsorption agent may be used.

It is an object of the present invention to provide a mineral composition for the prevention or treatment of magnesium imbalances or deficiencies or calcium/magnesium imbalances in an adult comprising calcium in the form of a bioavailable pharmaceutically acceptable salt thereof and magnesium in the form of a bioavailable pharmaceutically acceptable salt thereof, alone or in combination to achieve or maintain a molar ratio of ionized $Ca^{++}$/ionized $Mg^{++}$ of about 2.5:1–1:1, more preferably about 1.5:1, and most preferably about 2:1 in the blood or a molar ratio of ionized $Ca^{2+}$/ionized $Mg^{2+}$ of about 0.90:1 to 1.15:1, more preferable 0.92:1 to about 1.1:1, most preferably about 1:1 in cerebral spinal fluid.

It is an object of the present invention to provide a mineral composition for the prevention or treatment of magnesium deficiencies, magnesium imbalances and calcium/ magnesium imbalances based on the measured ionized level of $Mg^{2+}$ in whole blood, serum, plasma and other body fluids obtained by the method of the present invention using an ion selective electrode. If the measured ionized $Mg^{2+}$ in blood, serum or plasma is 0.5 mmol/l or less, then a bioavailable pharmaceutically acceptable magnesium salt which will result in a calculated dose of 400–600 mg/day of elemental magnesium should be given. Calcium should be administered in such a situation in the form of a bioavailable pharmaceutically acceptable calcium salt which will maintain the blood, plasma or serum level of ionized $Ca^{2+}$/ionized $Mg^{2+}$ in the molar ratio of about 2:1 after the ionized $Mg^{2+}$ level has been restored to the normal optimal level of about 0.58–0.60 mmol/l. If, however, the measured level of ionized $Mg^{2+}$ is between about 0.50.6 mmol/l, then a bioavailable pharmaceutically acceptable magnesium salt which will result in a calculated dose of 300 mg/day of element magnesium should be administered. Calcium, in this situation, should be administered in the form a of a bioavailable pharmaceutically acceptable calcium salt which will maintain the blood, plasma or serum level of ionized $Ca^{2+}$ lionized $Mg^{2+}$ in the molar ratio of about 2:1 after the ionized $Mg^{2+}$ level has been restored to the normal optimal level of about 0.58–0.60 mmol/l. For prevention of magnesium deficiencies and disease states which require a greater need for magnesium intake, a bioavailable pharmaceutically acceptable magnesium salt and a calcium salt which will result in calculated doses of approximately 200 mg of elemental magnesium and approximately 640 mg of elemental calcium, respectively, should be administered each day. This results in a molar ratio of calcium/magnesium of approximately 2:1.

It is a further object of the present invention to provide a mineral composition for prevention or treatment of magnesium deficiencies, magnesium imbalances, and calcium/magnesium imbalances based on the measured ionized level of $Mg^{2+}$ and ionized $Ca^{2+}$ in whole blood, serum plasma and other body fluids of a neonate, infant and child obtained by the method of the present invention using an ion selective electrode. Bioavailable pharmaceutically acceptable magnesium salt is administered to the neonate, infant and child in a concentration sufficient to attain or maintain the normal physiological ionized $Mg^{2+}$ levels in the blood. Bioavailable pharmaceutically acceptable calcium salt is administered in a concentration sufficient to maintain the blood, plasma, or serum level of ionized $Ca^{2+}$/ionized $Mg^{2+}$ in the molar ratio of about 1.9:1 to about 2.6:1, more preferably 2.3:1 to about 2.5:1, most preferably about 2.5:1 after t he ioni $Mg^{2+}$ level has been restored to the normal physiological level.

Bioavailable magnesium salts include conventional pharmaceutically acceptable organic and inorganic dietary supplement salts of magnesium such as magnesium oxide, magnesium phosphate, magnesium diphosphate, magnesium carbonate, magnesium aspartate, magnesium aspartate hydrochloride, magnesium chloride and the hydrates thereof, and the like. Bioavailable calcium salts include conventional pharmaceutically acceptable organic and inorganic dietary supplement salts of calcium such as dibasic calcium phosphate or the like.

One embodiment of the present invention relates to a solid oral dose form composition. The composition may be in the form of conventional pharmaceutical solid unit dosage forms such as a tablet, capsule, or sachet or the like, containing the magnesium and calcium components in the requisite ratio.

The bioavailable magnesium may be in a controlled release form wherein, upon ingestion, the magnesium is released into the gastrointestinal tract over a prolonged period of time or in an uncontrolled instant release form, or combination thereof.

In one embodiment, the bioavailable magnesium salt is released from the formulation at an average percent rate at least equal to the average percent rate of release of the calcium salt.

Preparation of the composition into a solid oral dose form along with pharmaceutically acceptable carriers and excipient are described in U.S. Pat. No. 4,954,349.

The present mineral composition may be given alone, as a dietary supplement, or may be administered with other minerals and/or with vitamins. One such multimineral dietary daily supplement includes, but is not limited to the following:

| Mineral | Approximate Elemental Concentration |
|---|---|
| Calcium (as Dibasic Calcium Phosphate) | 320–1280 mg |
| Magnesium (as Magnesium Sulfate) | 100–400 mg |
| Phosphorus (as Dibasic Calcium phosphate) | 125 mg |
| Iodine (as Potassium Iodide) | 150 ug |
| Iron (as Ferrous Fumarate) | 18 mg |
| Copper (as Cupric Oxide) | 2 mg |
| Zinc (as Zinc Oxide) | 15 mg |
| Manganese (as Manganese Sulfate) | 2.5 mg |
| Potassium (as Potassium Chloride) | 40 mg |
| Chloride (as Potassium Chloride) | 36.3 mg |
| Chromium (as Chromium Chloride) | 25 ug |
| Molybdenum (as Sodium Molybdate) | 25 ug |
| Selenium (as Sodium Selenite) | 25 ug |
| Vitamin K (as Phytonadione) | 25 ug |
| Nickel (as Nickelous Sulfate) | 5 ug |
| Tin (as Stannous Chloride) | 10 ug |
| Silicon (as Sodium Metasilicate) | 10 ug |
| Vanadium (as Sodium Metavanadate) | 10 ug |

The mineral composition of the present invention may also be administered with one or more of the following vitamins:

| Vitamin | Concentrations |
|---|---|
| Vitamin A (as Acetate and Beta Carotene) | 5000 I.U.[1] |
| Vitamin E (as dl-Alpha Tocopheryl Acetate) | 30 I.U. |
| Vitamin C (Ascorbic Acid) | 60 mg |
| Folic Acid | 0.4 |
| Vitamin B-1 (as Thiamine Mononitrate) | 1.5 mg |
| Vitamin B-2 (Riboflavin) | 1.7 mg |
| Niacin (Niacinamide) | 20 mg |
| Vitamin B-6 (as Pyridoxine HCl) | 2 mg |
| Vitamin B-12 (Cyanocobalamin) | 6 ug |
| Vitamin D (Calciferol) | 400 I.U. |
| Biotin | 30 ug |
| Pantothenic Acid (as Calcium Pantothenate) | 10 mg |

[1]I.U. = International Unit

A further aspect of the present invention is a $Ca^{2+}/Mg^{2+}$ mineral composition for use in an infant formula. The mineral composition provides a concentration of calcium and magnesium to ensure a ionized molar ratio of approximately 1.9 to about 2.6:1, more preferably 2.3:1 to about 2.5:1 of ionized $Ca^{2+}$: ionized $Mg^{2+}$.

An infant formula suitable for feeding neonates and infants comprises protein, carbohydrate, water, vitamins, minerals and an edible fat. The $Ca^{2+}/Mg^{2+}$ mineral composition for the infant formula contains between about 0.25 mmoles/kg/day to about 0.625 mmoles/kg/day of calcium in the form of a bioavailable pharmaceutically acceptable salt thereof, between about 0.1 mmoles/kg/day to about 0.25 mmoles/kg/day of magnesium in the form of a bioavailable pharmaceutically acceptable salt thereof, in order to achieve or maintain a molar ratio of ionized $Ca^{2+}$/ionized $Mg^{2+}$ in the blood of about 1.9 to about 2.6:1; more preferably 2.3:1 to about 2.5:1, most preferably about 2.5:1.

The other components in the infant formula and concentrations are provided in U.S. Pat. No. 4,670,285, and in: *Textbook of Gastroenterology and Nutrition in infancy* (2nd Ed) E. Lebenthal (Ed.) 1989, Raven Press, New York, N.Y. pp. 435–458 incorporated herein by reference.

It is understood that the examples and embodiments described herein are for illustrative purposes only and that various modifications or changes in light thereof will be suggested to persons skilled in the art and are to be included within the spirit and purview of this application and scope of the appended claims.

The references and patents referred to are incorporated herein by reference.

References

1. Stewart W F, Lipton R B, Celetano D D, Read M L. Prevalnce of migraine headache in the United States: relation to age, income, race and other sociodemographic factors. *JAMA* 1992; 267:64–69.
2. Featherstone H J. Migraine and muscle contraction headaches: a continuum. *Headache* 1985; 25:194–198.
3. Raskin N H, Appenzeller O. Headache. W B Saunders Co, Philadelphia, 1980.
4. Campbell J K. Comment on "migraine and tension-type headaches". *Clin J Pain* 1992; 8:37–38.
5. Altura B M. Calcium antagonist properties of magnesium: implications for antimigraine actions. *Magnesium* 1985; 4:169–175.
6. Ramadan N M, Halvorson H, Vande-Linde A, Levine S R, Helpern J A, Welch K M. Low brain magnesium in migraine. *Headache* 1989; 29:590–593.
7. Mody I, Lambert J D C, Heinemann V. Low extracellular magnesium induces epileptiform activity and spreading depression in rat hippocampal slices. *J Neurophysiol* 1987; 57:869–888.
8. Milner P M. Note on a possible correspondence between the scotomas of migraine and spreading depression of Leao. *Electroenceph Clin Neurophysiol* 1958; 10:705.
9. Simon K H. Magnesium: Physiologie, Pharmakologie, Kiinik. Wissenschaftliche Verlagsgesellschaft, Stuttgart, 1967.
10. Vosgerau H. Zur Behandlung der Migraine mit Magnesiumglutamat. *Therapie Gegenw* 1973; 112:640–648.
11. Weaver K. Magnesium and migraine; reversible hypomagnesic coagulative angiopathy, hypothesis and preliminary data (abstract). *J Am Coll Nutr* 1983; 2:287–288.
12. Facchinetti F, Sances G, Borella P, Genazzani A R, Nappi G. Magnesium prophylaxis of menstrual migraine: effects on intracellular magnesium. *Headache* 1991; 31:298–301.
13. Sarchielli P, Coata G, Firenze C, Morucci P, Abbritti G, Gallai V. Serum and salivary magnesium levels in migraine and tension-type headache. Results in a group of adult patients. *Cephalalgia* 1992; 112:21–27.
14. Schoenen 3, Sianard-Gainko J, Lenaerts M. Blood magnesium levels in migraine. *Cephalalgia* 1991, 11:97–99.
15. Galai V, Sarchielli P, Morucci P, Abbritti G. Magnesium content of mononuclear blood cells in migraine patients. *Headache* 1994; 34:160–165.
16. Altura B T, Shirly T, Young C C, Dell'Ofrano K, Handwerker S M, Altura B M. A new method for the rapid determination of ionized $Mg^{2+}$ in whole blood, serum and plasma. *Meth Find Exp Clin Pharmacol* 1992; 14(4):297–304.
17. Altura B T, Altura B M. Measurement of ionized magnesium in whole blood, plasma and serum with a new novel ion-selective electrode in healthy and diseased human subjects. *Magnesium Trace Elem* 1992; 10:90–98.
18. Altura B T, Shirey T L, Young C C, Dell'Ofrano K, Hiti J, Welsh R, Yeh Q, Barbour R L, Altura B M. Characterization of a new ion selective electrode for ionized magnesium in whole blood, plasma, serum and aqueous samples. *Scand J Clin Lab Invest* 1994; 54 (Suppl 217):21–36.
19. Mauskop A, Altura B T, Cracco R Q, Altura B M. Chronic daily headache—one disease or two. Diagnostic role of serum ionized magnesium. *Cephalalgia* 1994, 14:24–28.
20. Mauskop A, Altura B T, Cracco R Q, Altura B M. Serum ionized magnesium ($IMg^{2+}$) levels in patients (P) with episodic and chronic cluster headaches (CH). *Clin Pharm Ther* 53 (2):227, 1993 (Abstract).
21. Mauskop A, Altura B T, Cracco R Q, Altura B M. Deficiency in serum ionized Mg, but not total Mg in patients with migraine. Possible role of $ICa^{2+}/IMg^{2+}$ ratio. *Headache* 1993; 33(3): 135–138.
22. Mauskop A, Altura B T, Cracco R Q, Altura B M. Serum ionized magnesium levels in patients with tension-type headaches. In: Olesen J and Schoenen J, eds. Tension-type headache: classification, mechanisms and treatment. New York: Raven Press; 1993:137–140.
23. Anonymous. Headache Classification Committee of the International Headache Society. Classification and diagnostic criteria for headache disorders, cranial neuralgias and facial pain. *Cephalalgia* 1988;8, Suppl 7:10–73.
24. Pfaffenrath V, Isler H, Ekbom K. Chronic daily headache. *Cephalalgia* 1993; 13 (Suppl 12):66–67)
25. Sandrini G, Manzoni G C, Zanferrari C, Nappi G. An epidemiological approach to the nosography of chronic daily headache. *Cephalalgia* 1993;13 (Suppl 12):72–77.
26. Silberstein S D, Lipton R B, Solomon S, Mathew N T. Classification of daily and near-daily headaches: proposed revision to the IHS criteria. *Headache* 1994; 34:1–7.
27. Turlapaty P D M V, Altura B M. Magnesium deficiency produces spasms of coronary arteries: relationship to etiology of sudden death ischemic heart disease. *Science* 1980; 208:198–200.
28. Norman A B, Battaglia G, Creese I. [3H]WB4101 labels the 5-HT1A serotonin receptor subtype in rat brain. *Mol Pharmacol* 1985; 28:487–494.
29. Peters J A, Hales T G, Lambert J J. Divalent cations modulate 5-HT3 receptor-induced currents in N1E-115 neuroblastoma cells. *Eur J Pharmacol* 1988; 151:491–495.
30. Foster A C, Fagg G E. Neurobiology. Taking apart NMDA receptors. *Nature* 1987; 329–395:396.
31. Reynolds I J. Modulation of NMDA receptor responsiveness by neurotransmitters, drugs and chemical modification. *Life Sci* 1990; 47:1785–1792.
32. Huang Q F, Gebrewold A, Zhang A, Altura B T, Altura B M. Role of excitatory amino acids in regulation of rat pal microvasculature. *AM J Physiol* 1994; 266:R158-R163.
33. Zhang A, Altura B T, Altura B M. Endothelial-dependent sexual dimorphism in vascular smooth muscle: role of $Mg^{2+}$ and $Na^{2+}$. *Brit J Pharmacol* 1992; 105:305–310.
34. Seelig, M S. Magnesium Deficiency in the Pathogenesis of Disease. Plenum, New York, 1980.

35. Altura B M, Altura B T. Magnesium, electrolyte transport and coronary vascular tone. *Drugs* 1984; 28 (Suppl 1): 120–142.
36. Altura B M, Altura B T, Carella A, Murakawa T, Nishio A. $Mg^{2+}$–$Ca^{2+}$ interaction in contractility of vascular smooth muscle: $Mg^{2+}$ versus organic calcium channel blockers on myogenic tone and agonist-induced responsiveness of blood vessels. *Canad J Physiol Pharmacol* 1987;65:729–745.
37. White R E, Hartzell H C. Magnesium ions in cardiac function. Regulator of ion channels and second messengers. *Biochem Pharmacol* 1989; 38:859–867.
38. Altura B T, Altura B M. The role of magnesium in etiology of strokes and cerevrovasospasm. *Magnesium* 1982, 1:277–291.
39. Briel R C, Lippea T H, Zahradnik H P. Action of magnesium sulfate on platelet prostacyclin interaction and prostacyclin of blood vessels. *Am J Obstet Gynecol* 1985: 153: 232.
40. Hery M, Faudon M, Hery F. In vitro release of newly synthesized serotonin from superfused rat suprachiasmatic area-ionic dependency. *Eur J Pharmacol* 1983; 89:9–18.
41. Weglicki W B, Phillips T M. Pathobiology of magnesium deficiency: a cytokine/neurogenic inflammation hypothesis. *Am J Physiol* 1992, 263:R734–737.
42. Hanington E. The platelet and migraine. *Headache* 1986; 26:411–415.
43. Bevan J A (ed). Essentials of Pharmacology. Harper & Row, New York, 1969.
44. Carlson L A, Ekelund L-G, Oro L. Clinical and metabolic effects of different doses of prostaglandins $E_1$ in man. *Acta Med Scand* 1968; 183:423–430.
45. Altura B M, Altura B T. Vascular smooth muscle and prostaglandins. *Federation Proc* 1976; 35:2360–2366.
46. Moskowitz M A. The neurobiology of vascular head pain. Ann *Neurol* 1984; 16:157–168.
47. Shibata M, Bures J. Techniques for termination of reverberating spreading depression in rats. *J Neurophysiol* 1975; 38:158–166.
48. Altura B T. Type-A behavior and pattern and coronary vasospasm: a possible role of hypomagnesemia. *Med Hypoth* 1980; 6:753–757.
49. Altura B T, Wilmzig C, Trnovec T, Nyalassy S, Altura B M. Comparative effects of a Mg-enriched diet and different orally administered magnesium oxide preparations on ionized Mg, Mg metabolism and electrolytes in serum of human volunteers. *J Am Coll Nutrition* 1994; 13:447–454.
50. Zhang A, Cheng T P, Altura B T, Altura B M. M112+ and caffeine-induced intracellular $Ca^{2+}$ release in human vascular endothelial cells. *Brit J Pharmacol* 1993; 109: 291–292.
51. Zhang A, Cheng T P O, Altura, B M. Magnesium regulates intracellular free ionized calcium concentration and cell geometry in vascular smooth muscle cells. *Biochem Biophys Acta* 1992; 1134: 25–29.
52. Anderson K-E, Brandt L, Hindfelt B, Ryman L. Migraine treatment: with calcium channel blockers. *Acta Pharmacol Toxicol* 1986; 58 (Suppl 2):113–118.

What is claimed is:

1. A method of treating a headache in an individual having a serum ionized magnesium concentration of 0.44 mmoles/L to 0.53 mmoles/L, wherein said serum ionized magnesium concentration of said individual is below a normal serum ionized magnesium concentration range of 0.54 mmoles/L to 0.67 mmoles/L, said method consisting of:

administering to said individual having said serum ionized magnesium concentration of 0.44 mmoles/l to 0.53 mmoles/L and having at least one headache symptom, an amount of a water soluble magnesium salt, wherein said amount of said water soluble magnesium salt inhibits said at least one headache symptom in said individual within 24 hours and raises said serum ionized magnesium concentration in said individual to within said normal ionized magnesium concentration range of 0.54 mmoles/L to 0.67 mmoles/L.

2. The method of claim 1 wherein said at least one headache symptom is selected from the group consisting of: pain, aura, photophobia, nausea, unilateral pain, and phonophobia.

3. The method of claim 1 wherein the administration of said water soluble magnesium salt to said individual is performed by intravenous, subcutaneous, intramuscular, rectal, nasal, or aqueous oral administration.

4. The method of claim 1 wherein the administration of said water soluble magnesium salt is over a two-to-fifteen minute period and is provided intravenously.

5. The method of claim 1 wherein said water soluble magnesium salt is administered to said individual in more than one dose.

6. The method of claim 1 wherein said soluble water magnesium salt is selected from the group consisting of: magnesium sulfate, $MgSO_4.7H_2O$, $MgCl_2$, and $MgCl_2.6H_2O$.

7. The method of claim 1 wherein about 500 mg to about 5 grams of said water soluble magnesium salt is administered.

* * * * *